United States Patent [19]

Nestor, Jr. et al.

[11] Patent Number: 5,872,113
[45] Date of Patent: Feb. 16, 1999

[54] FLUORINATED VITAMIN D3 ANALOGS

[75] Inventors: John J. Nestor, Jr., Louisville, Ky.;
Percy S. Manchand, Montclair; Milan R. Uskokovic, Upper Montclair, both of N.J.; Brian H. Vickery, Los Altos Hills, Calif.

[73] Assignee: Syntex (U.S.A.) Inc., Palo Alto, Calif.

[21] Appl. No.: 857,569

[22] Filed: May 16, 1997

[51] Int. Cl.$^6$ .................. A61K 31/59; C07C 401/00; C07C 49/105; C07F 7/04

[52] U.S. Cl. ................. 514/167; 552/653; 556/463; 568/374

[58] Field of Search ................ 552/653; 514/167; 556/463; 568/374

[56] References Cited

U.S. PATENT DOCUMENTS

| | | | |
|---|---|---|---|
| 4,613,594 | 9/1986 | Baggiolini et al. | 514/167 |
| 5,087,619 | 2/1992 | Baggiolini et al. | 514/167 |
| 5,145,846 | 9/1992 | Baggiolini et al. | 514/167 |
| 5,384,314 | 1/1995 | Doran et al. | 514/167 |
| 5,428,029 | 6/1995 | Doran et al. | 514/167 |
| 5,451,574 | 9/1995 | Baggiolini et al. | 514/167 |

*Primary Examiner*—Deborah C. Lambkin
*Attorney, Agent, or Firm*—Rohan Peries

[57] ABSTRACT

Fluorinated Vitamin $D_3$ analogs, intermediates for their preparation, compositions comprising the analogs and methods of treatment of osteoporosis and related conditions with these and related analogs are provided.

27 Claims, 43 Drawing Sheets

IIa
Y= H or -SiMe₃

III

Ia

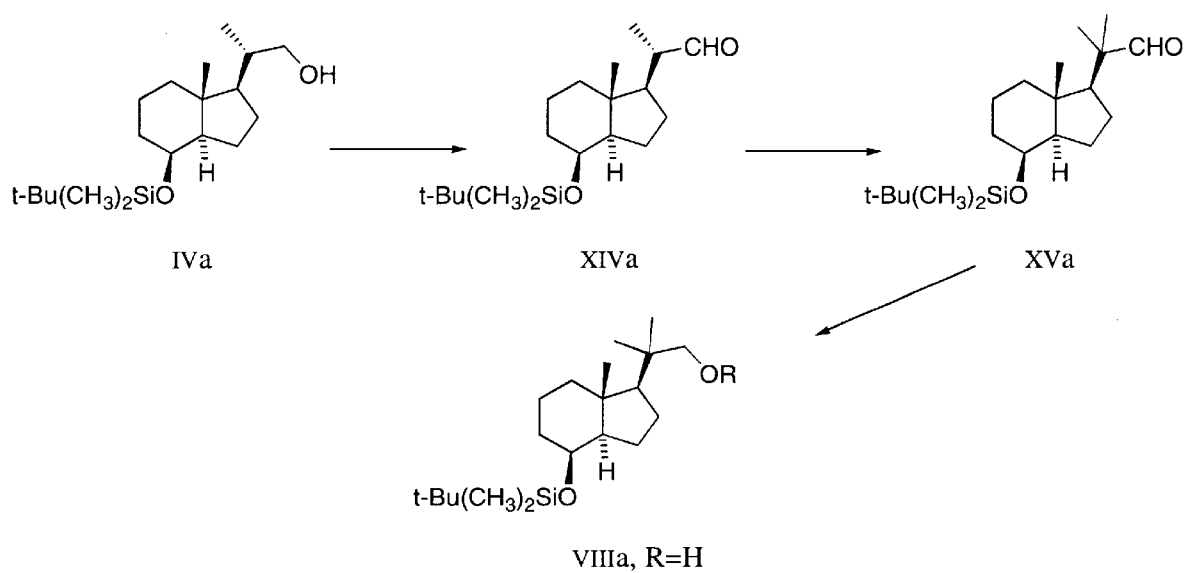

IIh
Y= H or -SiMe₃

III

Ih

XIIIa → XXXVIo → IIo (Y= H or -SiMe₃)

XIIIb → XXXVIp → IIp (Y= H or -SiMe₃)

XIIIc → XXXVIq → IIq (Y= H or -SiMe₃)

XIIId → XXXVIr → IIr (Y= H or -SiMe₃)

XIIIe → XXXVIs → IIs (Y= H or -SiMe₃)

XIIIf → XXXVIt → IIt (Y= H or -SiMe₃)

XIIIg → XXXVIu → IIu (Y= H or -SiMe₃)

XIIIv            XXXVI            IIw
Y= H or -SiMe$_3$

XIIIv    XXXVIz    IIz
Y= H or -SiMe₃

FLUORINATED VITAMIN D3 ANALOGS

BACKGROUND OF THE INVENTION a) Field of the Invention

This invention relates to fluorinated Vitamin $D_3$ analogs, compositions comprising the analogs and methods of treatment of osteoporosis and related conditions with these analogs.

b) Description of Related Art

Osteoporosis is the most common form of metabolic bone disease and may be considered the symptomatic, fracture stage of bone loss (osteopenia). Although osteoporosis may occur secondary to a number of underlying diseases, 90% of all cases appear to be idiopathic. Postmenopausal women are at risk for idiopathic osteoporosis (postmenopausal or Type I osteoporosis); another particularly high risk group for idiopathic osteoporosis is the elderly of either sex (senile or Type II osteoporosis). Osteoporosis has also been related to corticosteroid use, immobilization or extended bed rest, alcoholism, diabetes, gonadotoxic chemotherapy, hyperprolactinemia, anorexia nervosa, primary and secondary amenorrhea, transplant immunosuppression, and oophorectomy. Postmenopausal osteoporosis is characterized by fractures of the spine, while femoral neck fractures are the dominant features of senile osteoporosis.

The mechanism by which bone is lost in osteoporotics is believed to involve an imbalance in the process by which the skeleton renews itself. This process has been termed bone remodeling. It occurs in a series of discrete pockets of activity. These pockets appear spontaneously within the bone matrix on a given bone surface as a site of bone resorption. Osteoclasts (bone dissolving or resorbing cells) are responsible for the resorption of a portion of bone of generally constant dimension. This resorption process is followed by the appearance of osteoblasts (bone forming cells) which then refill with new bone the cavity left by the osteoclasts.

In a healthy adult subject, osteoclasts and osteoblasts function so that bone formation and bone resorption are in balance. However, in osteoporotics an imbalance in the bone remodeling process develops which results in bone being replaced at a slower rate than it is being lost. Although this imbalance occurs to some extent in most individuals as they age, it is much more severe and occurs at a younger age in postmenopausal osteoporotics, following oophorectomy, or in iatrogenic situations such as those resulting from corticosteroid therapy or the immunosuppression practiced in organ transplantation.

Various approaches have been suggested for increasing bone mass in humans afflicted with osteoporosis, including administration of androgens, fluoride salts, and parathyroid hormone and modified versions of parathyroid hormone. It has also been suggested that bisphosphonates, calcitonin, calcium, 1,25-dihydroxy vitamin $D_3$ and some of its analogs, and/or estrogens, alone or in combination, may be useful for preserving existing bone mass.

Hefti et al., *Clinical Science*, 62:389 (1982), describe studies using a high calcium diet supplemented with either parathyroid hormone or 1,25-$(OH)_2$ vitamin $D_3$ using normal and osteoporotic adult rats. The authors report that, although these studies showed an increase of whole-body calcium and skeletal mass, there was no restoration of individual trabeculae lost during the development of osteoporosis. Endo et al., *Nature*, 286:262 (1980), discuss the use of metabolites of vitamin D in conjunction with parathyroid hormone (PTH) to stimulate bone formation in vitro. However, these treatments with PTH and 1,25-$(OH)_2$ vitamin $D_3$ were no more effective than PTH alone in stimulating re-calcification of bone.

Rader et al., *Calcified Tissue International*, 29(1):21 (1979), describe the treatment of thyroparathyroidectomized rats with dietary calcium and intraperitoneal injection of a parathyroid extract. Although this treatment stimulated 1,25-$(OH)_2$ vitamin $D_3$ production and effected a marked increase in bone mineralization, it was also found to produce bone resorption as evidenced by the appearance of cavities in the cortical bone. There was no effect on rates of bone formation, or bone matrix apposition. Wong et al., *Surgical Forum*, 30:100 (1979), teach the administration to thyroparathyroidectomized dogs of daily intramuscular parathyroid extract or oral 1,25-$(OH)_2$ vitamin $D_3$ simultaneously with thyroid replacement therapy. The effect of these treatments on absorption of dietary calcium is discussed in the context of parathyroidism although not in the context of osteoporosis.

Peacock et al., *Vitamin D Proceedings Workshop.*, E. Norman, Ed., p. 411 (1977), disclose the inhibition by calcitonin and steroid sex hormones of the resorptive effect of vitamin D metabolites and parathyroid hormone on mouse calvaria bone in tissue culture. Pechet et al., *American Journal of Medicine*, 43(5):696 (1967), teach that minimum levels of parathyroid hormone are necessary in order for vitamin D to exert its effects on bone resorption rather than bone formation. In Mahgoub et al., *Biochemical and Biophysical Research Communications*, 62:901 (1975), the authors state that active vitamin D metabolites (25-OH vitamin $D_3$ and 1,25-$(OH)_2$ vitamin $D_3$) potentiate the ability of parathyroid hormone to elevate the cyclic AMP levels of cultured rat fetal bone cells.

Vitamin $D_3$ is a critical element in the metabolism of calcium, promoting intestinal absorption of calcium and phosphorus, maintaining adequate serum levels of calcium and phosphorus, and stimulating flux of calcium into and out of bone. The D vitamins are hydroxylated in vivo, with the resulting 1α,25-dihydroxy metabolite being the active material. Animal studies with 1,25-$(OH)_2$ vitamin D have suggested bone anabolic activity. Aerssens et al. in Calcif Tissue mnt, 55:443–450 (1994) reported upon the effect of 1α-hydroxy Vitamin $D_3$ on bone strength and composition in growing rats with and without corticosteroid treatment. However, human usage is restricted to antiresorption due to the poor therapeutic ratio (hypercalciuria and hypercalcemia as well as nephrotoxicity).

Dechant and Goa, in "Calcitriol. A review of its use in the treatment of postmenopausal osteoporosis and its potential in corticosteroid-induced osteoporosis", *Drugs Aging* (NEW ZEALAND) 5(4):300–17 (1994), reported that 1,25-dihydroxyvitamin $D_3$ (calcitriol) has shown efficacy in the treatment of postmenopausal osteoporosis (and promise in corticosteroid-induced osteoporosis) based upon a clinical trial in 622 women with postmenopausal osteoporosis. Patients with mild to moderate disease (but not those with more severe disease) who received calcitriol (0.25 microgram twice daily) had a significant 3-fold lower rate of new vertebral fractures after 3 years of treatment, compared with patients receiving elemental calcium 1000 mg/day. In patients commencing long term treatment with prednisone or prednisolone, calcitriol 0.5 to 1.0 micrograms/day plus calcium 1000 mg/day, administered with or without intranasal calcitonin 400 IU/day, prevented steroid-induced bone loss. Overall, calcitriol was well tolerated. At recommended dosages hypercalcaemia was infrequent and mild, generally responding to reductions in calcium intake and/or calcitriol dosage. The narrow therapeutic window of calcitriol required that its use be adequately supervised, with periodic monitoring of serum calcium and creatinine levels. This study clearly identifies the key limitation of calcitriol therapy as the close proximity of therapeutic and toxic doses.

Baggiolini et al. in European Patent Publication No. 580,968 disclose fluorinated vitamin $D_3$ analogs, including 1α-fluoro-25-hydroxy-16-ene-23-yne-26,27-hexafluorochole-calciferol, useful for the treatment of hyperproliferative disorders of the skin, for the treatment of cancer and leukemia, and for the treatment of sebaceous gland diseases. U.S. patent application Ser. No. 08/560,080 discloses and claims the use of this compound for the restoration of bone mass and/or density in osteoporosis. The disclosures of the cited references are hereby incorporated by reference.

The 1α-fluoro analogs of Vitamin $D_3$ disclosed herein have not previously been described, nor has their use in the treatment of osteoporosis been recognized.

SUMMARY OF THE INVENTION

This invention provides fluorinated Vitamin $D_3$ analogs of the Formula (I):

(I)

wherein:

X is hydrogen or =CH2;

$R_1$ and R2 are, independently of each other, hydrogen, ($C_1$–$C_4$) alkyl or fluoroalkyl, or $R_1$ and $R_2$ together with C-20 form a ($C_3$–$C_6$) cycloalkyl or cyclofluoroalkyl, or $R_1$ and $R_2$ together form =$CH_2$;

$R_3$ and $R_4$ are, independently of each other, a ($C_1$–$C_4$) alkyl or fluoroalkyl, or $R_3$ and $R_4$ together with C-25 form a ($C_3$–$C_9$) cycloalkyl or cyclofluoroalkyl;

A is a single bond or a double bond; and

B is a double bond or a triple bond; except that:

(i) when X is =$CH_2$, $R_3$ and $R_4$ are each $CF_3$, A is a double bond and one of $R_1$ or $R_2$ is hydrogen, then the other of $R_1$ or $R_2$ cannot be $CH_3$;

(ii) when X is =$CH_2$, $R_3$ and $R_4$ are each a ($C_1$–$C_2$) alkyl, A is a double bond and $R_2$ is hydrogen, then $R_1$ cannot be $CH_3$;

(iii) when X is =$CH_2$, $R_3$ and $R_4$ are each a ($C_1$–$C_4$) alkyl, A is a double bond and $R_1$ is hydrogen, then $R_2$ cannot be $CH_3$;

(iv) when X is =$CH_2$, one of $R_3$ or $R_4$ is a $CF_3$, A is a double bond, $R_1$ is $CH_3$ and $R_2$ is hydrogen, then the other of $R_3$ or $R_4$ cannot be $CH_3$; and (v) when X is hydrogen, $R_3$ and $R_4$ are each $CF_3$, A is a double bond, B is a triple bond and $R_2$ is hydrogen, then $R_1$ cannot be $CH_3$.

This invention also provides compositions comprising a pharmaceutically acceptable carrier and a fluorinated Vitamin $D_3$ analog of Formula (I), as defined above.

The present invention further provides a method for treating osteoporosis via administration of a compound of Formula (I), wherein X is hydrogen or =$CH_2$, $R_1$ and $R_2$ are, independently of each other, hydrogen, ($C_1$–$C_4$) alkyl or fluoroalkyl, or $R_1$ and $R_2$ together with C-20 form a ($C_3$–$C_6$) cycloalkyl or cyclofluoroalkyl, or $R_1$ and $R_2$ together form =$CH_2$, $R_3$ and $R_4$ are, independently of each other, ($C_1$–$C_4$) alkyl or fluoroalkyl, or $R_3$ and $R_4$ together with C-25 form a ($C_3$–$C_9$) cycloalkyl or cyclofluoroalkyl, A is a single bond or a double bond and B is a double bond or a triple bond; except that where $R_3$ and $R_4$ are each $CF_3$, A is a double bond, B is a triple bond and $R_2$ is hydrogen, then $R_1$ cannot be $CH_3$, in an amount therapeutically effective to restore bone density to an asymptomatic level, without inducing hypercalciuria, hypercalcemia, or nephrotoxicity.

BRIEF DESCRIPTION OF THE DRAWINGS

The preparations of compounds of Formula (I) and the key intermediates required for their synthesis are illustrated by the following figures:

FIGS. 1, 2 & 2a illustrate the synthesis of the 20-methyl analog (Ia) of 1α-fluoro-25-hydroxy-23-yne-26,27-hexafluoro-cholecalciferol and intermediates (IIa) and (VIIIa) used in the preparation of (Ia), respectively.

DETAILED DESCRIPTION OF THE INVENTION

Figure 1:
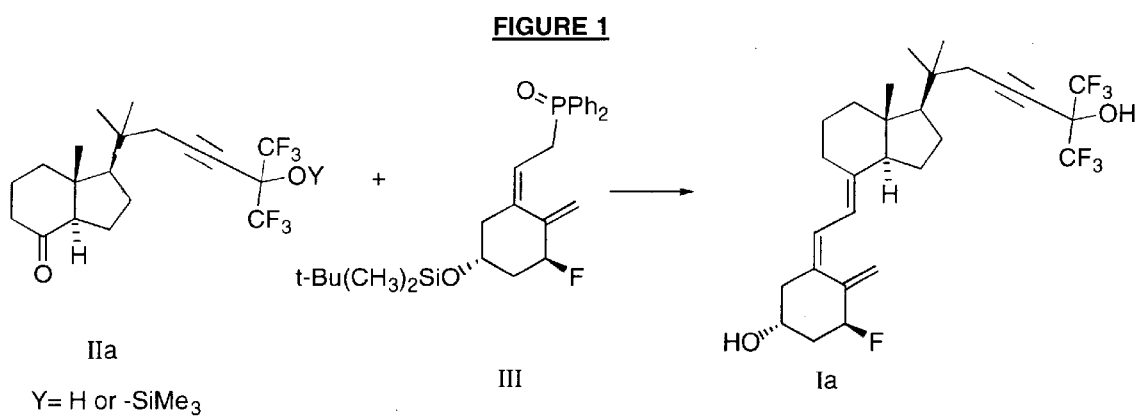

The fluorinated Vitamin $D_3$ analog of the present invention have the following general structure:

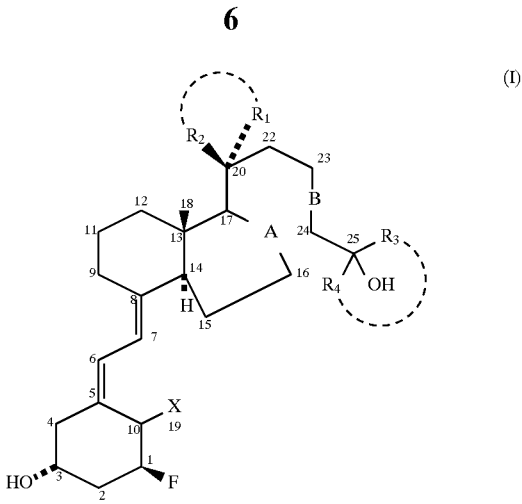

wherein:

X is hydrogen or $=CH_2$;

$R_1$ and $R_2$ are, independently of each other, hydrogen, ($C_1$–$C_4$) alkyl or fluoroalkyl, or $R_1$ and $R_2$ together with C-20 form a ($C_3$–$C_6$) cycloalkyl or cyclofluoroalkyl, or $R_1$ and $R_2$ together form $=CH_2$;

$R_3$ and $R_4$ are, independently of each other, a ($C_1$–$C_4$) alkyl or fluoroalkyl, or $R_3$ and $R_4$ together with C-25 form a ($C_3$–$C_9$) cycloalkyl or cyclofluoroalkyl;

A is a single bond or a double bond; and

B is a double bond or a triple bond; except that:

(i) when X is $=CH_2$, $R_3$ and $R_4$ are each $CF_3$, A is a double bond and one of $R_1$ or $R_2$ is hydrogen, then the other of $R_1$ or $R_2$ cannot be $CH_3$;

(ii) when X is $=CH_2$, $R_3$ and $R_4$ are each a ($C_1$–$C_2$) alkyl, A is a double bond and $R_2$ is hydrogen, then $R_1$ cannot be $CH_3$;

(iii) when X is $=CH_2$, $R_3$ and $R_4$ are each a ($C_1$–$C_4$) alkyl, A is a double bond and $R_1$ is hydrogen, then $R_2$ cannot be $CH_3$;

(iv) when X is $=CH_2$, one of $R_3$ or $R_4$ is a $CF_3$, A is a double bond, $R_1$ is $CH_3$ and $R_2$ is hydrogen, then the other of $R_3$ or $R_4$ cannot be $CH_3$; and (v) when X is hydrogen, $R_3$ and $R_4$ are each $CF_3$, A is a double bond, B is a triple bond and $R_2$ is hydrogen, then $R_1$ cannot be $CH_3$.

The method of the present invention for treating osteoporosis is via administration of a compound of Formula (I), wherein:

X is hydrogen or $=CH$;

$R_1$ and $R_2$ are, independently of each other, hydrogen, ($C_1$–$C_4$) alkyl or fluoroalkyl, or $R_1$ and $R_2$ together with C-20 form a ($C_3$–$C_6$) cycloalkyl or cyclofluoroalkyl, or $R_1$ and $R_2$ together form $=CH_2$;

$R_3$ and $R_4$ are, independently of each other, ($C_1$–$C_4$) alkyl or fluoroalkyl, or $R_3$ and $R_4$ together with C-25 form a ($C_3$–$C_9$) cycloalkyl or cyclofluoroalkyl;

A is a single bond or a double bond; and

B is a double bond or a triple bond;

except that when $R_3$ and $R_4$ are each $CF_3$, A is a double bond, B is a triple bond and R is hydrogen, then $R_1$ cannot be $CH_3$, in an amount therapeutically effective to restore bone density to an asymptomatic level, without inducing hypercalciuria, hypercalcemia, or nephrotoxicity.

As used herein, the term ($C_1$–$C_4$) alkyl means a fully-saturated hydrocarbon radical having from one to four carbon atoms; a $(C_1-C_4)$ fluoroalkyl is an alkyl radical, as defined above, in which one or more hydrogen atoms attached to the carbon backbone have been replaced with one or more fluorine atoms. A $(C_3-C_6)$ cycloalkyl means a cyclic saturated hydrocarbon radical having from three to six carbon atoms, a $(C_3-C_6)$ cyclofluoroalkyl means a cycloalkyl radical, as defined above, in which one or more hydrogen atoms attached to the carbon backbone have been replaced with one or more fluorine atoms. A $(C_3-C_9)$ cycloalkyl is a cyclic saturated hydrocarbon radical having from three to nine carbon atoms; a $(C_3-C_9)$ cyclofluoroalkyl is a cyclic saturated hydrocarbon radical having from three to nine carbon atoms in which one or more hydrogen atoms attached to the carbon backbone have been replaced with one or more fluorine atoms.

Also as used herein, cyclopropano means a cyclopropane radical; cyclodifluoropropano means a cyclopropane radical substituted with two fluorine atoms; cyclotetrafluoropropano means a cyclopropane radical substituted with four fluorine atoms; cyclopentano means a fully-saturated five-carbon ring radical; cyclodifluoropentano means a saturated five-carbon ring radical substituted with two fluorine atoms; cyclotetrafluoropentano means a saturated five-carbon ring radical substituted with four fluorine atoms; cyclohexafluoropentano means a saturated five-carbon ring radical substituted with six fluorine atoms; cyclooctafluoropentano means a saturated five-carbon ring radical substituted with eight fluorine atoms; cyclohexano means a fully-saturated six-carbon ring radical; cyclodifluorohexano means a saturated six-carbon ring radical substituted with two fluorine atoms; cyclotetrafluorohexano means a saturated six-carbon ring radical substituted with four fluorine atoms; cyclohexafluorohexano means a saturated six-carbon ring radical substituted with six fluorine atoms; cyclooctafluorohexano means a saturated six-carbon ring radical substituted with eight fluorine atoms.

Further as used herein, by double bond it is meant an unsaturated linkage between two adjacent carbon atoms in which two pairs of electrons are shared equally, and wherein each carbon atom bears two single-bonded substituents in either a Z (zusammen) or an E (entgegen) configuration about the double bond.

The compounds disclosed herein have not previously been described, nor has their use in the treatment of osteoporosis recognized.

Nomenclature

The compounds of the present invention may be generically described as 1α-fluoro analogs of vitamin $D_3$ (cholecalciferol). Hence, the compounds of the invention are named using the vitamin $D_3$ numbering system as illustrated in FIG. (A) below.

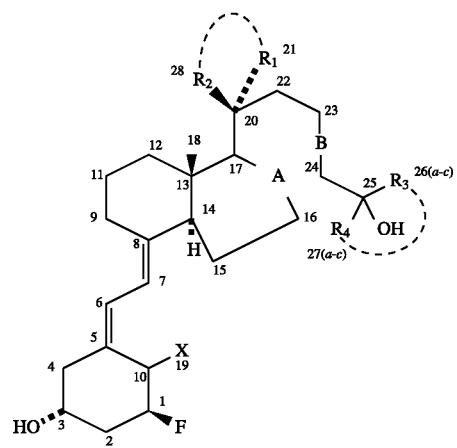

Fig.(A)

For example, a compound of the invention where $R_1$ is hydrogen, $R_2$ is $CH_3$, A is a double bond, B is a triple bond and $R_3$ is $CF_3$ is named as 1α-fluoro-25-(RS)-hydroxy-16-ene-23-yne-26-trifluoro-20-epi-cholecalciferol.

The following table provides some representative examples of compounds of the present invention:

| Cpd # | A | B | $R_1$ | $R_2$ | $R_3$ | $R_4$ | X |
|---|---|---|---|---|---|---|---|
| 1 | = | ≡ | $CH_3$ | $CH_3$ | $CH_2CH_3$ | $CH_2CH_3$ | $=CH_2$ |
| 2 | = | ≡ | H | $CH_3$ | $CH_2CH_3$ | $CH_2CH_3$ | H |
| 3 | = | ≡ | $CH_3$ | H | $CH_2CH_3$ | $CH_2CH_3$ | H |
| 4 | = | ≡ | $CH_2-CH_2$ | | $CH_2CH_3$ | $CH_2CH_3$ | $=CH_2$ |
| 5 | = | ≡ | $CF_2-CF_2$ | | $CH_2CH_3$ | $CH_2CH_3$ | $=CH_2$ |
| 6 | = | ≡ | $CF_2-CH_2$ | | $CH_2CH_3$ | $CH_2CH_3$ | $=CH_2$ |
| 7 | = | ≡ | $CH_2-CF_2$ | | $CH_2CH_3$ | $CH_2CH_3$ | $=CH_2$ |
| 8 | = | ≡ | $CF_3$ | $CF_3$ | $CH_2CH_3$ | $CH_2CH_3$ | $=CH_2$ |
| 9 | = | ≡ | H | $CF_3$ | $CH_2CH_3$ | $CH_2CH_3$ | $=CH_2$ |
| 10 | = | ≡ | $CF_3$ | H | $CH_2CH_3$ | $CH_2CH_3$ | $=CH_2$ |
| 11 | = | ≡ | $CH_3$ | $CH_3$ | $CH_3$ | $CH_3$ | $=CH_2$ |
| 12 | = | ≡ | $CH_3$ | $CH_3$ | $CF_3$ | $CF_3$ | $=CH_2$ |
| 13 | = | ≡ | $CH_3$ | $CH_3$ | $CH_2CF_3$ | $CH_2CF_3$ | $=CH_2$ |
| 14 | = | ≡ | $CH_3$ | $CH_3$ | $CF_2CH_3$ | $CF_2CH_3$ | $=CH_2$ |
| 15 | = | ≡ | $CH_3$ | $CH_3$ | $CF_2CF_3$ | $CF_2CF_3$ | $=CH_2$ |
| 16 | — | ≡ | $CH_3$ | $CH_3$ | $CH_2CH_3$ | $CH_2CH_3$ | $=CH_2$ |
| 17 | — | ≡ | $CH_2-CF_2$ | | $CF_2CH_3$ | $CF_2CH_3$ | $=CH_2$ |
| 18 | — | ≡ | H | $CF_3$ | $CF_2CF_3$ | $CF_2CF_3$ | $=CH_2$ |
| 19 | = | trans C=C bond | $CH_3$ | $CH_3$ | $CH_2CH_3$ | $CH_2CH_3$ | $=CH_2$ |
| 20 | — | trans C=C bond | $CH_2-CH_2$ | | $CF_3$ | $CF_3$ | $=CH_2$ |
| 21 | = | cis C=C bond | $CH_3$ | $CH_3$ | $CH_2CF_3$ | $CH_2CF_3$ | $=CH_2$ |
| 22 | — | cis C=C bond | $CF_2-CH_2$ | | $CH_2CH_3$ | $CH_2CH_3$ | $=CH_2$ |
| 23 | = | ≡ | $CH_3$ | $CH_3$ | $CH_2CH_3$ | $CH_2CH_3$ | H |
| 24 | — | trans C=C bond | H | $CF_3$ | $CF_2CH_3$ | $CF_2CH_3$ | H |
| 25 | = | ≡ | $CH_2$ | | $CH_2CH_3$ | $CH_2CH_3$ | $=CH_2$ |
| 26 | — | ≡ | $CH_2$ | | $CF_3$ | $CF_3$ | H |
| 27 | = | ≡ | $CH_3$ | $CH_3$ | $CH_2-CH_2$ | | $=CH_2$ |
| 28 | = | ≡ | $CF_3$ | H | $CF_2-CF_2$ | | $=CH_2$ |
| 29 | = | ≡ | $CF_2-CF_2$ | | $CF_2-CF_2$ | | $=CH_2$ |

-continued

| Cpd # | A | B | $R_1$ | $R_2$ | $R_3$ | $R_4$ | X |
|---|---|---|---|---|---|---|---|
| 30 | = | ≡ | $CH_3$ | $CH_3$ | $CF_2CF_2$—$CF_2CF_2$ | | $=CH_2$ |
| 31 | = | ≡ | $CH_2$ | | $CF_2CF_2$—$CF_2CF_2$ | | $=CH_2$ |
| 32 | — | cis C=C bond | $CH_2$ | | $CH_2CF_2$—$CH_2CF_2$ | | H |
| 33 | = | ≡ | $CF_3$ | $CF_3$ | $CF_3$ | $CF_3$ | $=CH_2$ |
| 34 | = | ≡ | $CH_3$ | $CF_3$ | $CH_3$ | $CH_3$ | $=CH_2$ |
| 35 | — | ≡ | H | $CH_3$ | $CH_3$ | $CF_3$ | $=CH_2$ |
| 36 | — | ≡ | $CH_3$ | $CH_3$ | $CF_3$ | $CF_3$ | $=CH_2$ |
| 37 | — | cis C=C bond | $CH_3$ | $CH_3$ | $CF_3$ | $CF_3$ | $=CH_2$ |
| 38 | = | trans C=C bond | $CH_3$ | $CH_3$ | $CH_2CF_3$ | $CH_2CF_3$ | $=CH_2$ |
| 39 | — | ≡ | $CH_3$ | $CH_3$ | $CF_3$ | $CF_3$ | H |
| 40 | — | ≡ | $CH_2$—$CH_2$ | | $CF_3$ | $CF_3$ | $=CH_2$ |
| 41 | = | ≡ | $CH_2$—$CH_2$ | | $CH_2CH_2$—$CH_2CH_2$ | | $=CH_2$ |
| 42 | = | ≡ | $CH_2$—$CF_2$ | | $CF_2CF_2$—$CF_2CF_2$ | | $=CH_2$ |
| 43 | — | trans C=C bond | $CH_2$ | | $CH_2CH_2$—$CH_2CH_2$ | | $=CH_2$ |
| 44 | — | cis C=C bond | $CF_2$—$CF_2$ | | $CH_2$—$CH_2$ | | H |
| 45 | — | ≡ | $CH_2$ | | $CH_2CH_2$—$CH_2CH_2$ | | $=CH_2$ |
| 46 | = | ≡ | $CH_2$ | | $CF_2$—$CF_2$ | | $=CH_2$ |
| 47 | = | trans C=C bond | $CH_2$—$CH_2$ | | $CH_2$—$CH_2$ | | H |
| 48 | = | ≡ | $CH_2$—$CF_2$ | | $CF_2$—$CF_2$ | | $=CH_2$ |
| 49 | — | ≡ | $CH_3$ | $CH_3$ | $CH_3$ | $CF_3$ | $=CH_2$ |
| 50 | = | ≡ | H | $CH_3$ | $CH_2CH_3$ | $CH_3$ | H |
| 51 | = | ≡ | $CH_3$ | $CF_3$ | $CF_3$ | $CH_2CF_3$ | $=CH_2$ |
| 52 | — | ≡ | $CF_3$ | $CF_3$ | $CH_3$ | $CF_2CF_3$ | H |
| 53 | — | trans C=C bond | $CH_2$—$CH_2$ | | $CF_2CF_3$ | $CF_3$ | $=CH_2$ |
| 54 | = | cis C=C bond | $CH_2$—$CF_2$ | | $CF_3$ | $CH_2CH_3$ | H |
| 55 | = | ≡ | $CH_2$ | | $CF_3$ | $CH_3$ | H |
| 56 | = | ≡ | H | $CH_3$ | $CF_3$ | $CH_3$ | $=CH_2$ |
| 57 | = | trans C=C bond | H | $CH_3$ | $CF_3$ | $CH_3$ | $=CH_2$ |
| 58 | — | ≡ | $CH_2$—$CH_2$ | | $CH_3$ | $CH_3$ | $=CH_2$ |
| 59 | = | ≡ | H | $CH_3$ | $CH_2CH_2$—$CH_2CH_2$ | | $=CH_2$ |
| 60 | — | trans = bond | $CH_2$—$CH_2$ | | $CF_3$ | $CF_3$ | $=CH_2$ |
| 61 | — | ≡ | $CH_2$—$CH_2$ | | $CF_3$ | $CF_3$ | $=CH_2$ | and are named as:

56. 1-α-Fluoro-25(RS)-hydroxy-16-ene-23-yne-26-trifluoro-20-epi-cholecalciferol.
57. 1-α-Fluoro-25(RS)-hydroxy-16,23E-diene-26-trifluoro-20-epi-cholecalciferol. $[\alpha]_D^{25}$ =+75.5° (c 0.2, EtOH); UV (MeOH) :λmax 206nm (ε17325), 243 (13485), 268 (13189).
58. 1-α-Fluoro-25-hydroxy-23-yne-20,21,28-cyclopropyl-cholecalciferol.
59. 1-α-Fluoro-25-hydroxy-16-ene-23-yne-25,26,27-cyclopentyl-20-epi-cholecalciferol. $[\alpha]_D^{25}$ =+60.5° (c 0.2, CHCl$_3$)
60. 1-α-Fluoro-25-hydroxy-23E-ene-26,27-hexafluoro-20,21,28-cyclopropyl-cholecalciferol.
61. 1-α-Fluoro-25-hydroxy-23-yne-26,27-hexafluoro-20,21,28-cyclopropyl-cholecalciferol.

General Synthesis

Analogs of this invention may generally be prepared by reaction and combination of fragments of Vitamin D$_3$ molecules (see e.g., Shiuey et al., *J. Org. Chem*, 55:243 (1990); Wovkulich, P. M. et al., *Tetrahedron*, 40, 2283 (1984); Doran et al., U.S. Pat. No. 5,428,029; and Baggiolini et al., U.S. Pat. No. 5,451,574). The starting materials and reagents used in preparing these compounds are either available from commercial suppliers such as Aldrich Chemical Co., (Milwaukee, Wis.), or Sigma (St. Louis, Mo.) or they can be prepared by methods known to those skilled in the art following procedures set forth in references such as Fieser and Fieser's *Reagents for Organic Synthesis*, Vol. 1–15 (John Wiley and Sons, 1991); March's *Advanced Organic Chemistry*, (John Wiley and Sons 4th Edition) and Larock's *Comprehensive Organic Transformations* (VCH Publishers Inc., 1989).

The preparation of compounds of Formula I and the intermediates used in their preparation is illustrated by the reaction schemes as shown in the Drawings.

23-Yne Analogs a. Synthesis of the 20-methyl analog (I*a*) of 1α-fluoro-25-hydroxy-23-yne-26,27-hexafluoro-cholecalciferol is illustrated in FIG. 1, and described in Example 1, below.

Figure 2:
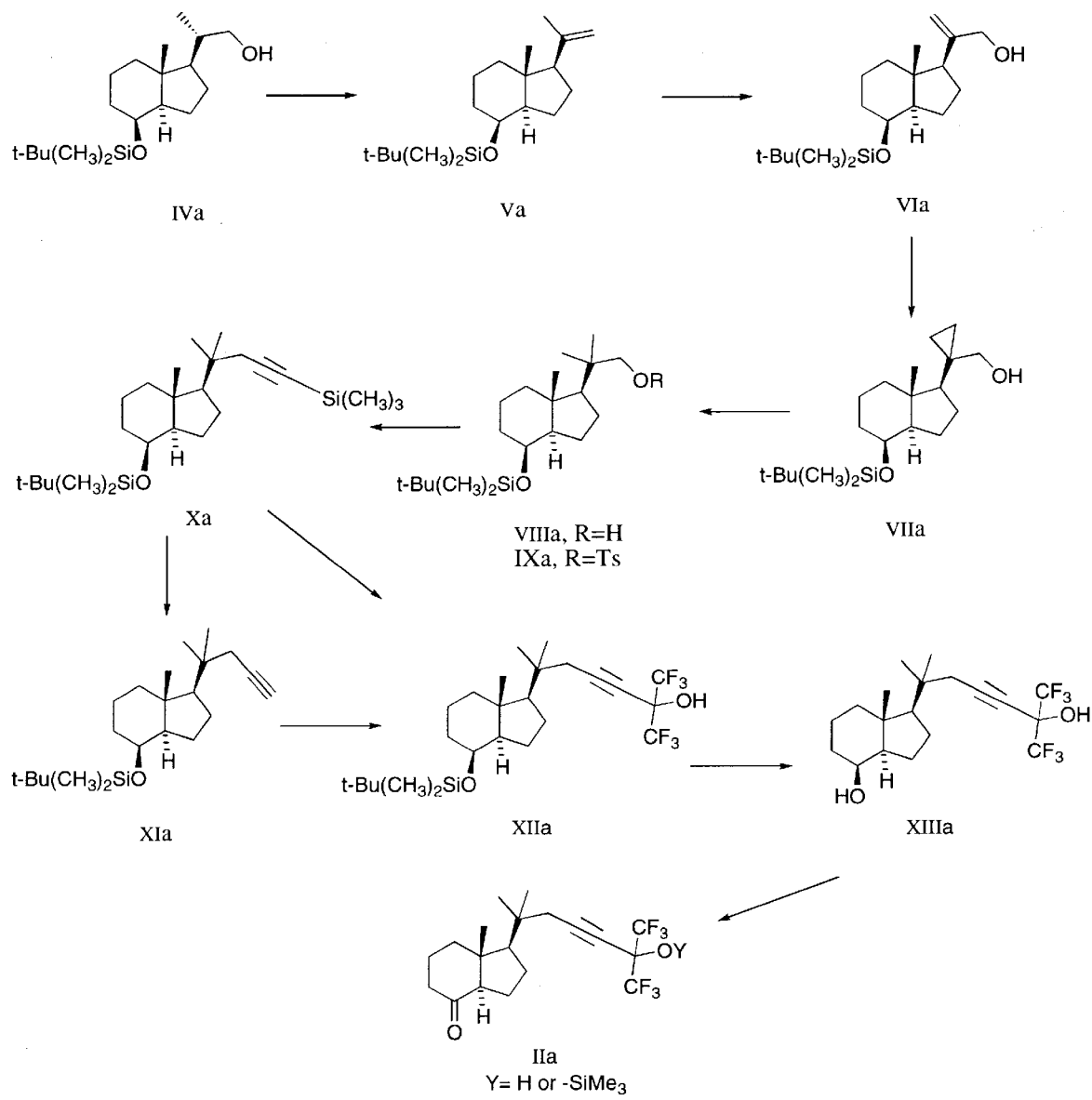

The key intermediate II*a* where Y is hydrogen or -SiMe$_3$ can be prepared according to the synthesis described in FIG. 2, starting from the known compound IV*a*. Dehydration of IV*a* by known methods produces the ene product V*a*, which can be selectively oxidized with selenium dioxide to the allylic alcohol VI*a*. Cyclopropanation by standard methods gives the cyclopropyl alcohol VII*a*, which on hydrogenation produces the desired dimethyl intermediate VIII*a*. Extension of the side chain with the acetylene fragment can be performed by a previously known procedure consisting of displacement of the tosyloxy group in IX*a* with lithium trimethylsilyl acetylide. The completion of the side chain can be accomplished by treatment of the lithium acetylide derived from X*a* or XI*a* with hexafluoroacetone. Removal of the silyl protective group and oxidation completes the synthesis of the desired compound II*a* where Y is hydrogen. Compound II*a* where Y is hydrogen can be converted to the corresponding trimethylsilyl ether derivative (Y=-SiMe$_3$), if desired, by reacting it with a suitable silylating agent such as 1-trimethylsilylimidazole in an aprotic organic solvent such as methylene chloride.

Figure 3:
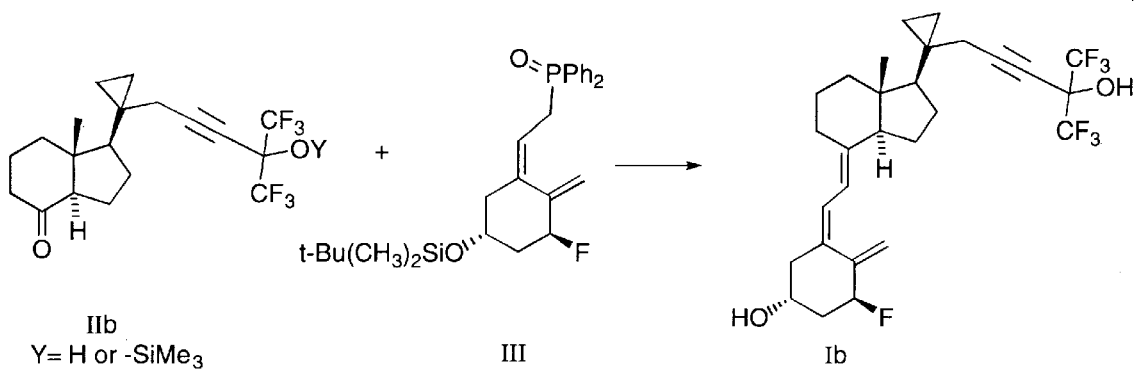
FIGS. 3, 4 & 4a illustrate the synthesis of the 20-cyclopropyl analog (Ib) of 1α-fluoro-25-hydroxy-23-yne-26,27-hexafluoro-cholecalciferol and intermediates (IIb) and (Xb) used in the preparation of (Ib), respectively.

The intermediate VIII*a* in the synthesis of the compound II*a* (FIG. 2) can also be obtained from the same starting material IV*a* using an alternative process described in FIG. 2*a*. The aldehyde XIV is methylated by standard methods, and thus obtained dimethyl aldehyde XV*a* is reduced to VIII*a*.

b. Synthesis of the 20-cyclopropyl analog (I*b*) of 1α-fluoro-25-hydroxy-23-yne-26,27-hexafluoro-cholecalciferol is illustrated in FIG. 3 and described in Example 2.

Figure 4:
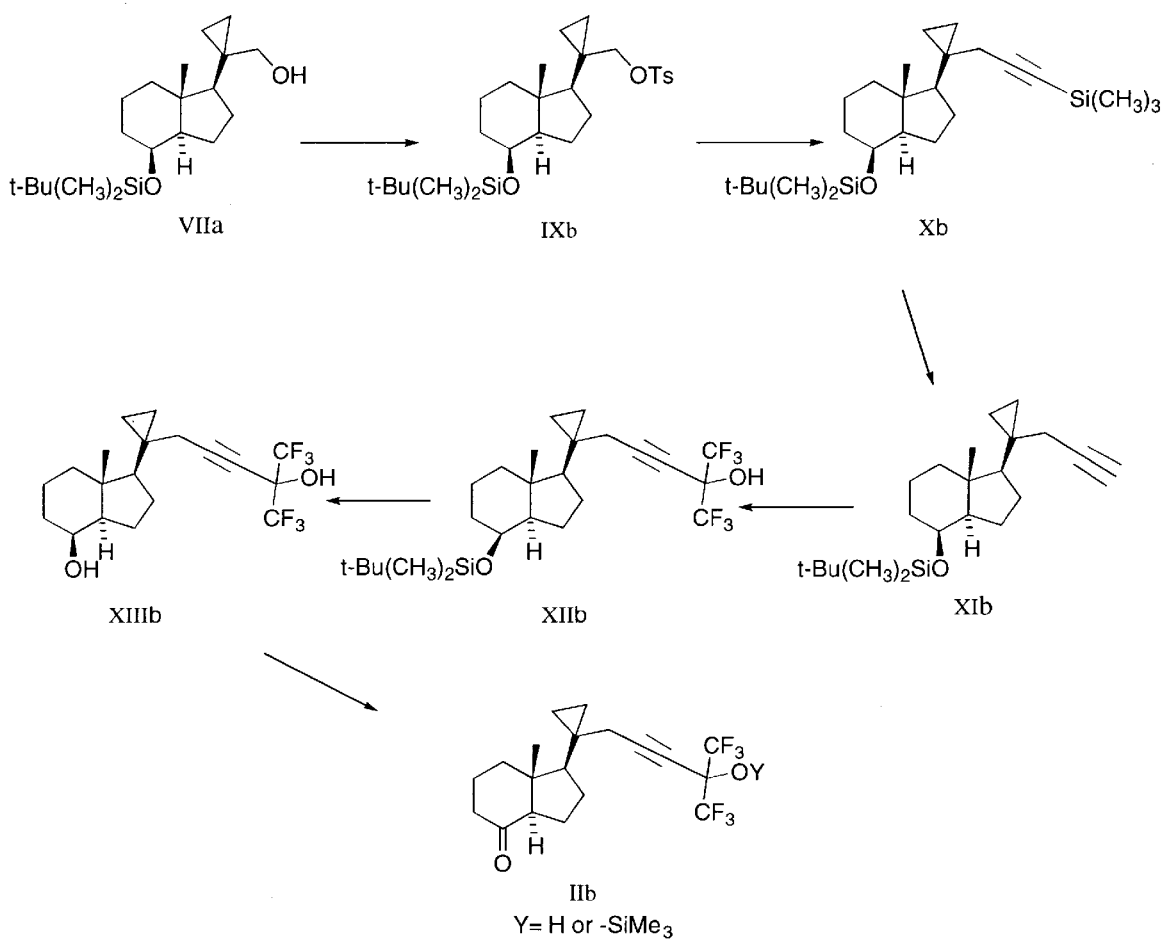

The key intermediate II*b* where Y is hydrogen or -SiMe$_3$ can be obtained from the cyclopropyl alcohol VII*a*, already described in FIG. 2. This synthesis of II*b* is shown in FIG. 4, and it is in accordance with the process shown in FIG. 2 for the synthesis of II*a*. Anal. data for II*b* (Y=hydrogen): mp 145°–146° C.; $[\alpha]_D^{25}$=–8.52° (c 0.704, EtOH); MS m/z 396.

Figure 4A:
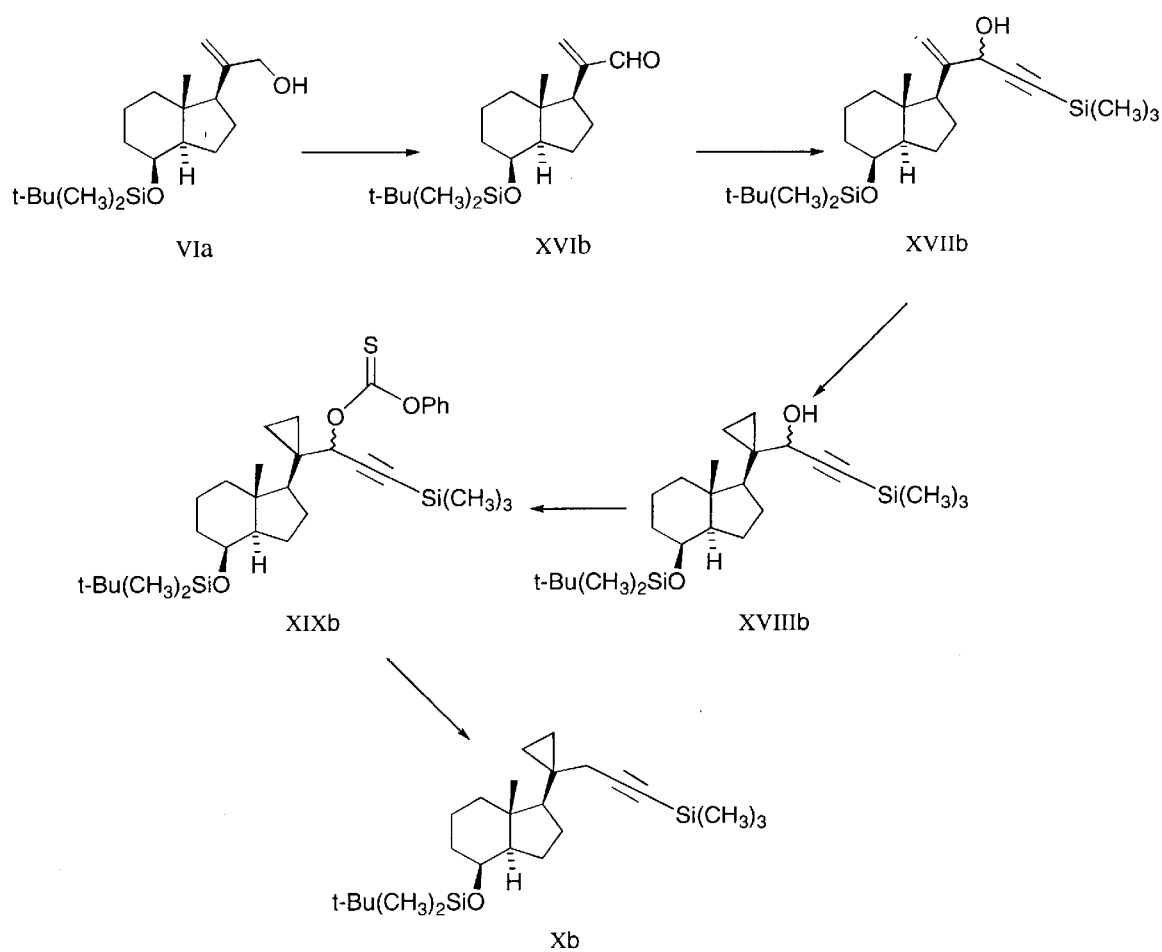
Figure 5:
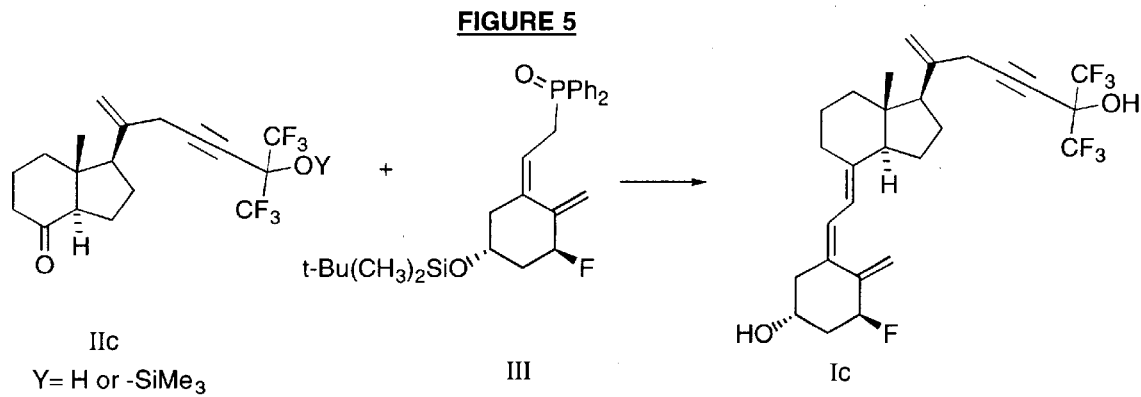
FIGS. 5, 6 & 6a illustrate the synthesis of the 20-ene analog (Ic) of 1α-fluoro-25-hydroxy-23-yne-26,27-hexafluoro-cholecalciferol and intermediates (IIc) and (IXc) used in the preparation of (Ic), respectively.

An alternative pathway to the intermediate X*b* in FIG. 4 is also possible. It consists of using the allylic alcohol VI*a* (FIG. 2) as a starting material and it is illustrated in FIG. 4a. Oxidation by standard methods gives the unsaturated aldehyde XVI*b*, which upon treatment with lithium trimethylsilyl acetylide gives the epimeric allylic propargylic alcohols XVII*b*. Cyclopropanation will lead selectively to the cyclopropyl alcohols XVIII*b*, which on Barton deoxygenation gives the desired X*b*, precursor of II*b*.

c. Synthesis of the 20-ene analog (I*c*) of 1α-fluoro-25-hydroxy-23-yne-26,27-hexafluoro-cholecalciferol is illustrated in FIG. 5, and described in Example 3.

Figure 6:
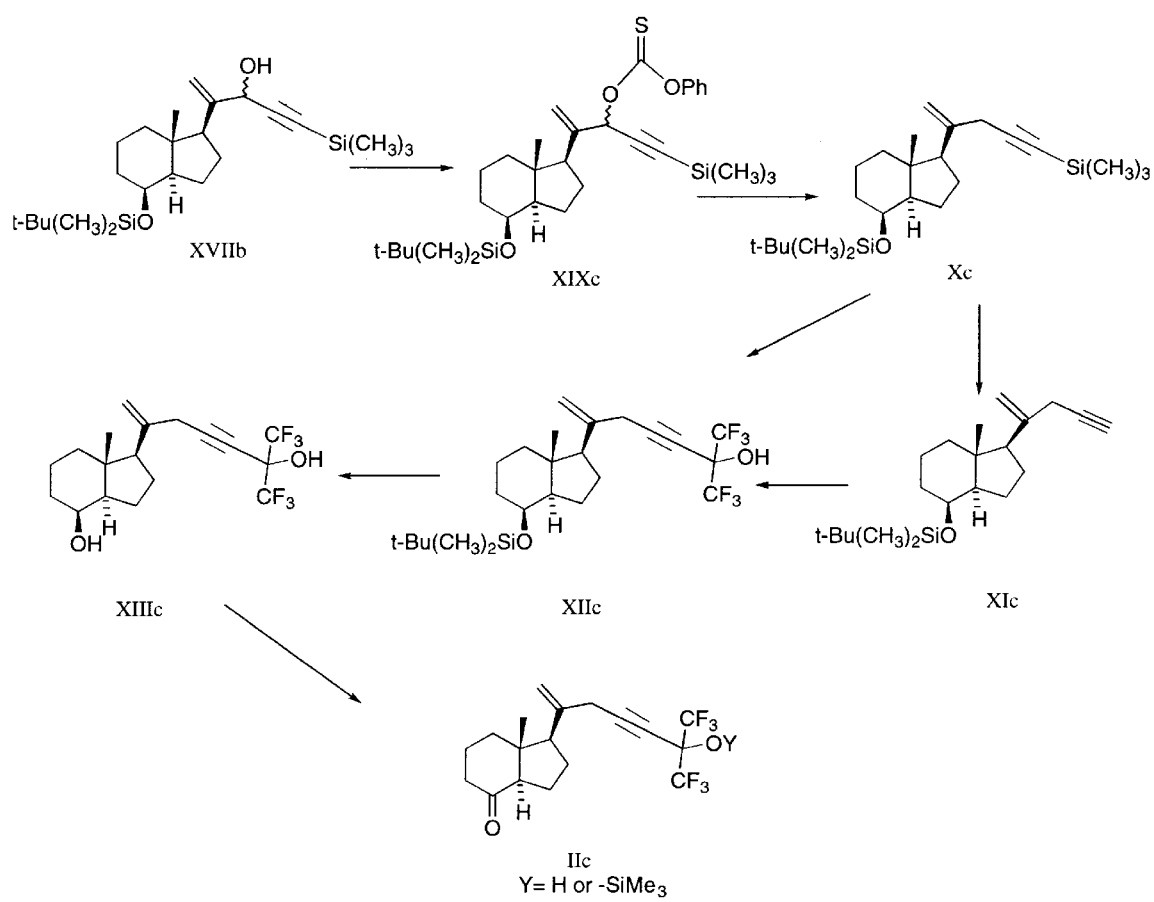

In this case, the key intermediate II*c* where Y is hydrogen or -SiMe$_3$ can be synthesized from the epimeric allylic-propargylic alcohols XVII*b* (FIG. 4a) according to the process outlined in FIG. 6. Barton deoxygenation produces in this case the ene-yne feature of the desired side chain, compound X*c*. The lithium acetylide derived from X*c* or XI*c* reacts with hexafluoroacetone to complete the side chain as in XII*c*. Removal of the silyl protecting group and oxidation produces the desired ketone II*c* (Y=hydrogen) which can be converted to the corresponding trimethylsilyl ether derivative (Y=-SiMe$_3$), if desired, as described above.

Figure 6A:
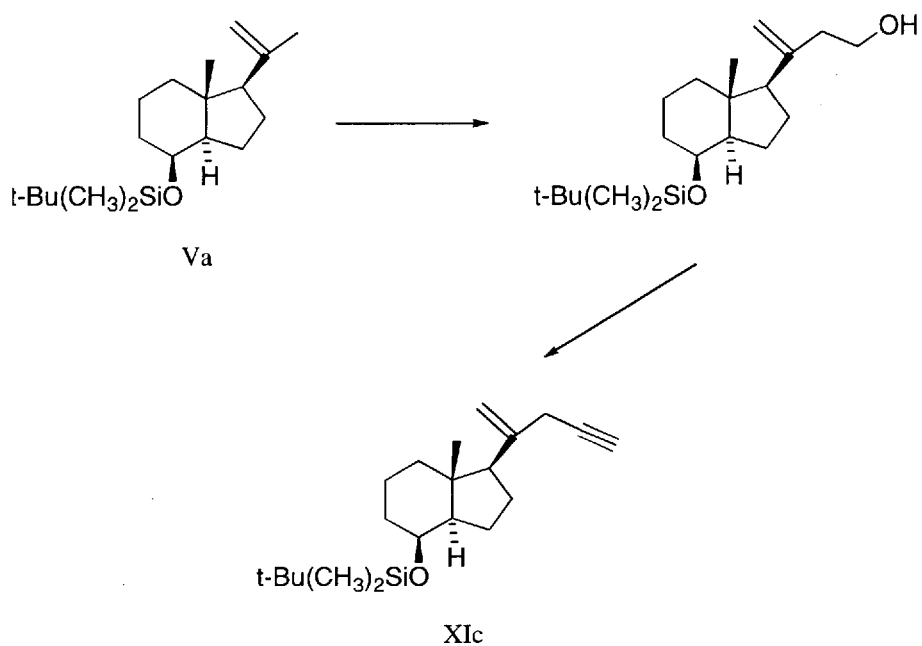
Figure 7:
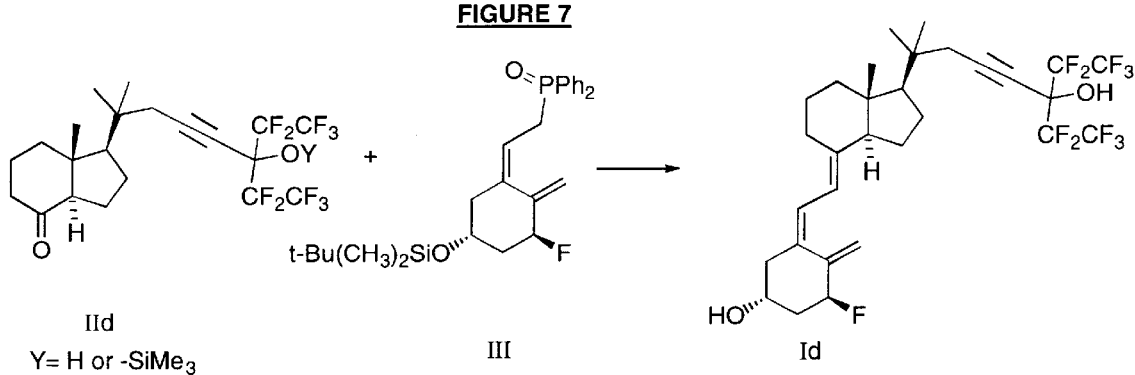
FIGS. 7 & 8 illustrate the synthesis of the 20-methyl-26,27-bishomo-26,26a,27,27a-decafluoro analog (Id) of 1α-fluoro-25-hydroxy-23-yne-cholecalciferol and intermediates (IId) used in the preparation of (Id), respectively.

The ene-yne intermediate XI*c* (FIG. 6) can be also obtained from the early ene-precursor V*a* (FIG. 2) as shown in FIG. 6a. An ene-reaction with formaldehyde produces the C-23 homo-allylic alcohol, from which the acetylene XI*c* can be constructed in two steps by known methods.

d. Synthesis of the 20-methyl-26,27-bishomo-26,26a,27,27a-decafluoro analog (I*d*) of 1α-fluoro-25-hydroxy-23-yne-cholecalciferol is illustrated in FIG. 7, and described in Example 4.

Figure 8:
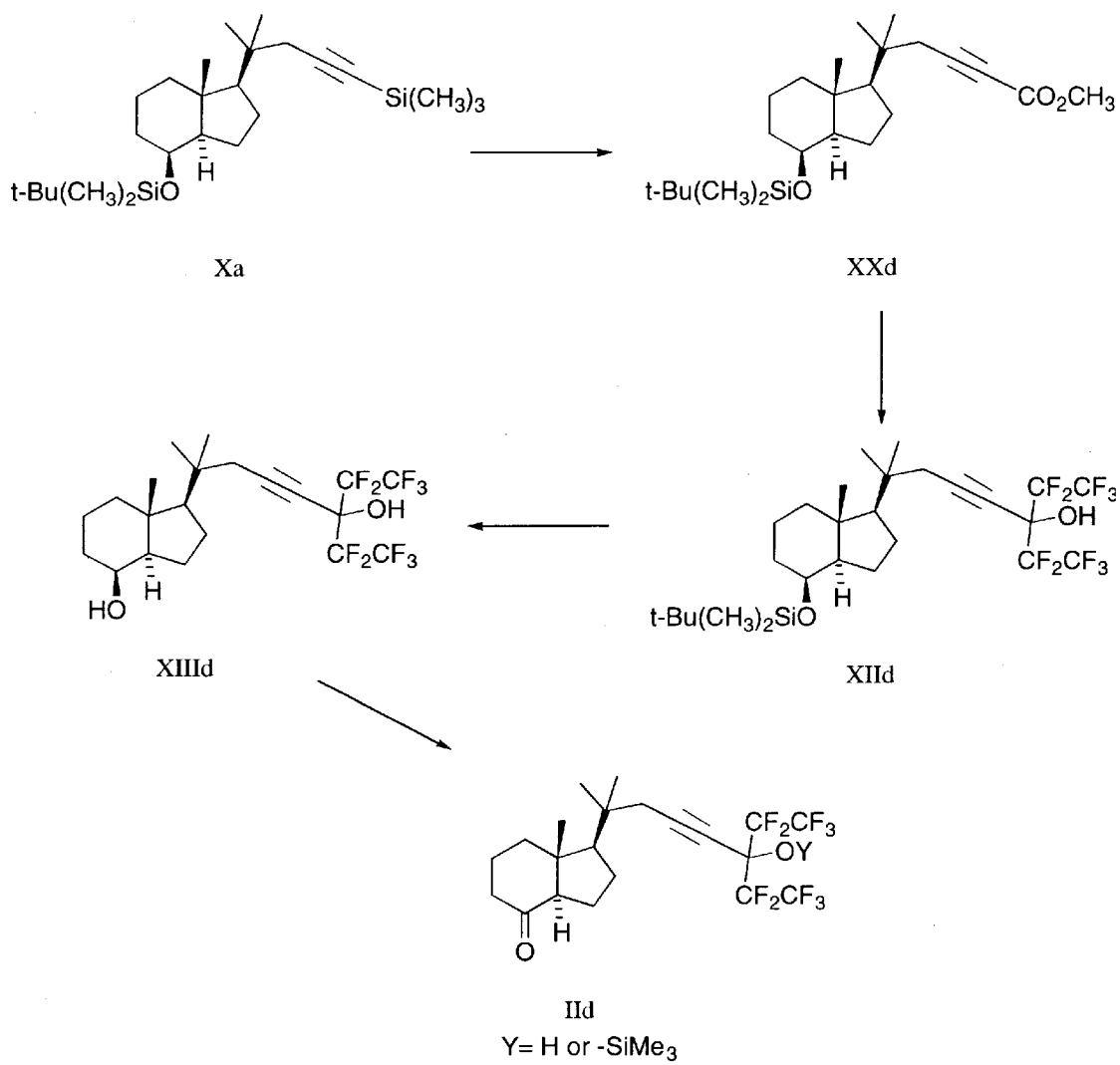

The key intermediate decafluoro-hydroxy-ketone II*d* where Y is hydrogen or -SiMe$_3$ can be synthesized according to the process illustrated in FIG. 8. This synthesis starts from the previously cited silylated 20-methyl-acetylene X*a* (FIG. 2), which is first extended to the carboxylic ester XX*d*. Reaction with pentafluoroethyl lithium produces the complete side chain, the tertiary alcohol XII*d*. Removal of the protecting silyl group and oxidation gives compound II*d* (Y=hydrogen) which can be converted to the corresponding trimethylsilyl ether derivative (Y=-SiMe$_3$), if desired, as described previously.

Figure 9:
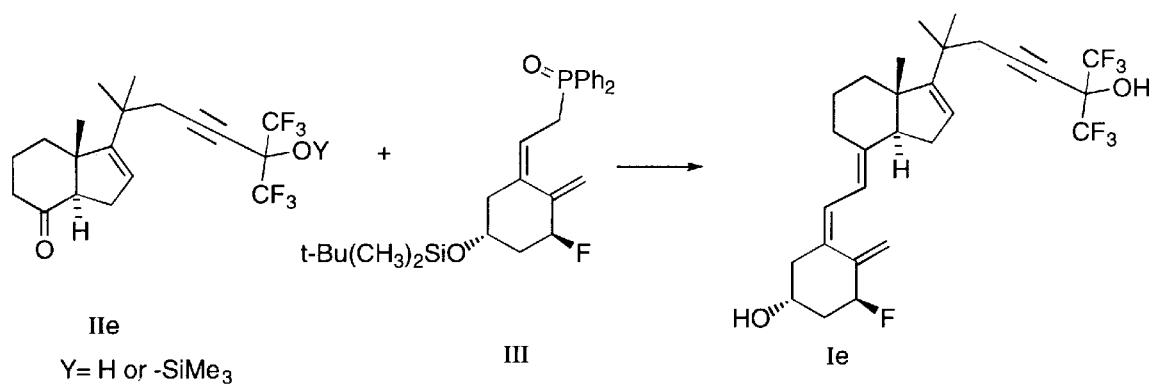
FIGS. 9 & 10 illustrate the synthesis of the 20-methyl analog (Ie) of 1α-fluoro-25-hydroxy-16-ene-23-yne-26,27-hexafluoro-cholecalciferol and intermediates (IIe) used in the preparation of (Ie), respectively.

16-Ene-23-yne-Analogs e. Synthesis of the 20-methyl analog (I*e*) of 1α-fluoro-25-hydroxy-16-ene-23-yne-26,27-hexafluoro-cholecalciferol is illustrated in FIG. 9, and described in Example 5.

Figure 10:
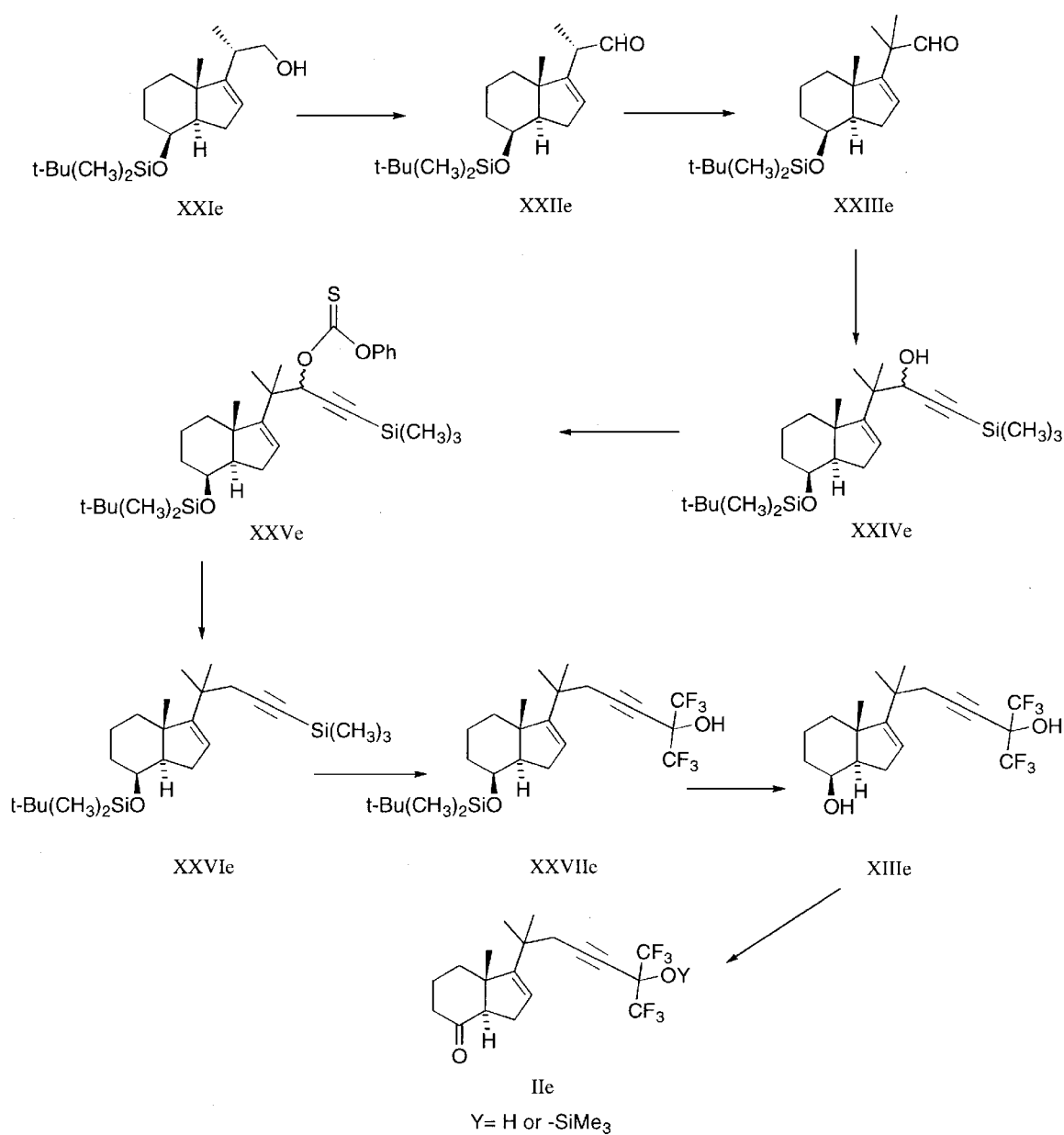
Figure 11:
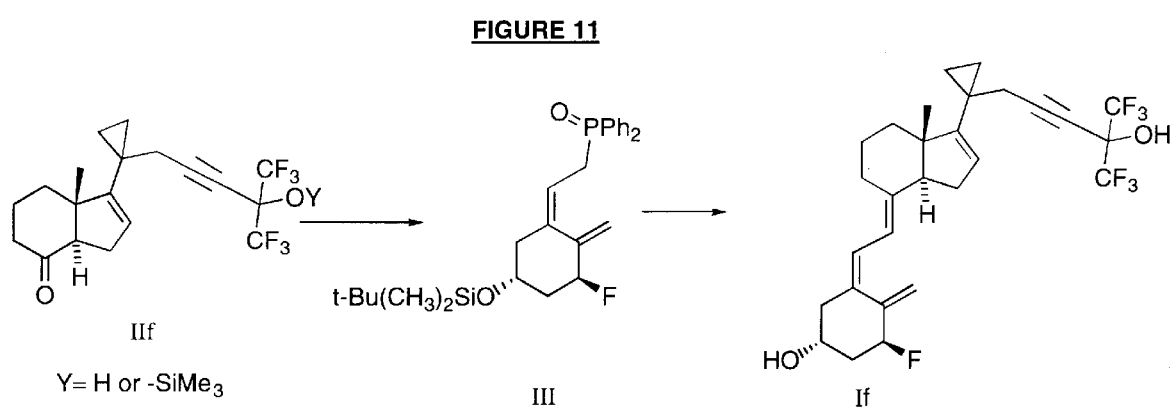
FIGS. 11 & 12 illustrate the synthesis of the 20-cyclopropyl analog (If) of 1α-fluoro-25-hydroxy-16-ene-23-yne-26,27-hexafluoro-cholecalciferol and intermediates (IIf) used in the preparation of (If), respectively.

The key intermediate II*e* where Y is hydrogen or -SiMe$_3$ can be synthesized as shown in FIG. 10. This synthesis starts with the known monosilylated diol XXI*e*, which on oxidation produces the aldehyde XXII*e*. Alkylation of this aldehyde forms the dimethyl analog XXIII*e*, which upon treatment with lithium trimethylsilyl acetylide produces the epimeric propargylic alcohols XXIV*e*. Barton deoxygenation gives the trimethylsilyl acetylene XXVI*e*. Lithium acetylide derived from XXVI*e* in a reaction with hexafluoroacetone produces the complete side chain XXVII*e*. Removal of the silyl protecting group and oxidation lead to the desired intermediate II*e* (Y=hydrogen) which can be converted to the corresponding trimethylsilyl ether derivative (Y=-SiMe$_3$) as described previously.

f. Synthesis of the 20-cyclopropyl analog (I*f*) of 1α-fluoro-25-hydroxy-16-ene-23-yne-26,27-hexafluoro-cholecalciferol is illustrated in FIG. 11, and described in Example 6.

Figure 12:
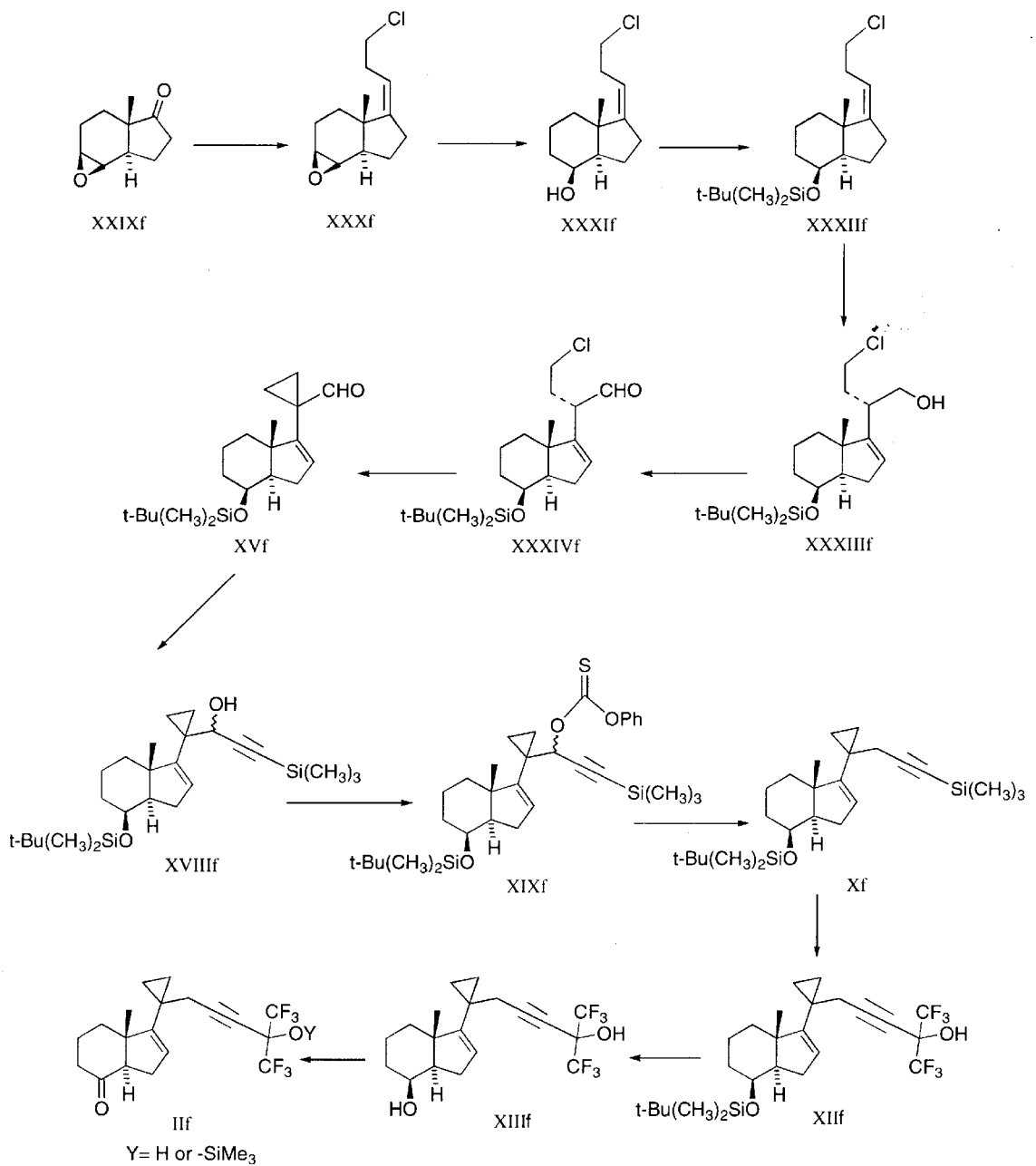
Figure 13:
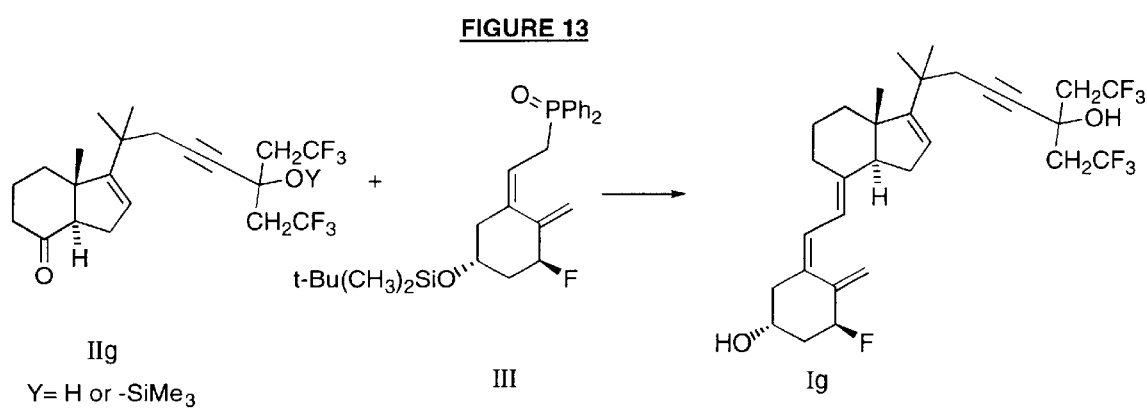
FIGS. 13 & 14 illustrate the synthesis of the 20-methyl-26,27-bishomo-26a,27a-hexafluoro analog (Ig) of 1α-fluoro-25-hydroxy-16-ene-23-yne-cholecalciferol and intermediates (IIg) used in the preparation of (Ig), respectively.

The key intermediate II*f* where Y is hydrogen or -SiMe$_3$ can be synthesized from the known epoxy-ketone XXIX*f* according the process shown in FIG. 12. The attachment of the incipient three carbons of the side chain by a Wittig reaction, reduction of the epoxide, protection of thus formed hydroxy group as a silyl ether, insertion of the C-20 aldehyde via an ene reaction oxidation, and cyclization of the cyclopropyl ring gives a compound of formula XV*f*. Completion of the II*f* synthesis is according to the process described in FIGS. 4a and 4 for the saturated analog II*b*.

g. Synthesis of the 20-methyl-26,27-bishomo 26a,27a-hexafluoro analog (I*g*) of 1α-fluoro-25-hydroxy-16-ene-23-yne-cholecalciferol is illustrated in FIG. 13, and described in Example 7.

Figure 14:
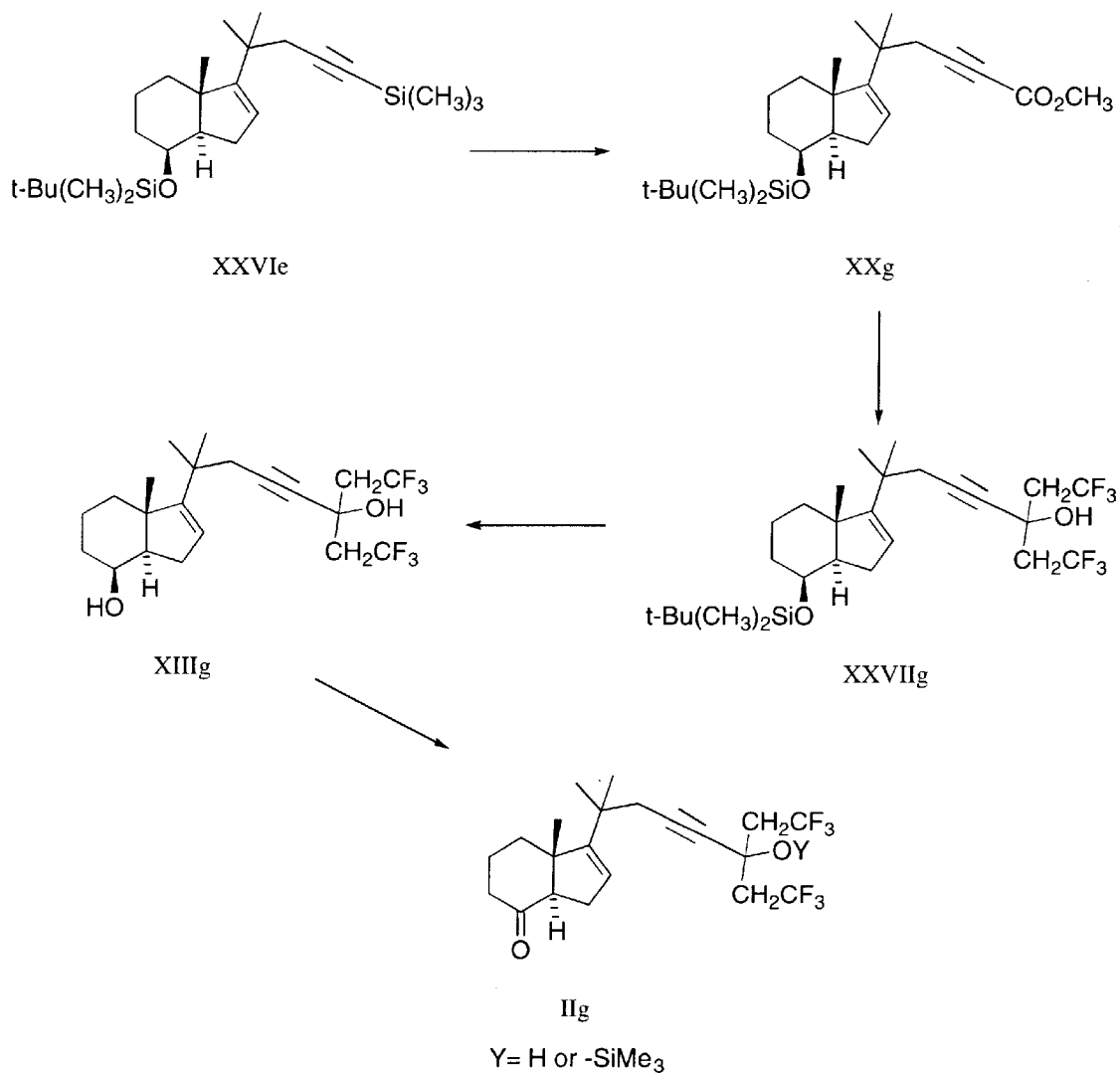

The key intermediate II*g* where Y is hydrogen or -SiMe$_3$ can 4i9 be prepared from the previously cited compound XXVI*e* (FIG. 10) according to the process outlined in FIG. 14. Extension of the side chain of XXVI*e* gives the propargylic ester XX*g*, which is then converted to the tertiary alcohol XXVII*g* in a reaction with trifluoroethyl lithium. Removal of the silyl protecting group and oxidation produces the ketone II*g* (Y=hydrogen) which can be converted to the corresponding trimethylsilyl ether derivative (Y=-SiMe$_3$) as described above.

23Z-Ene Analogs

Figure 15:
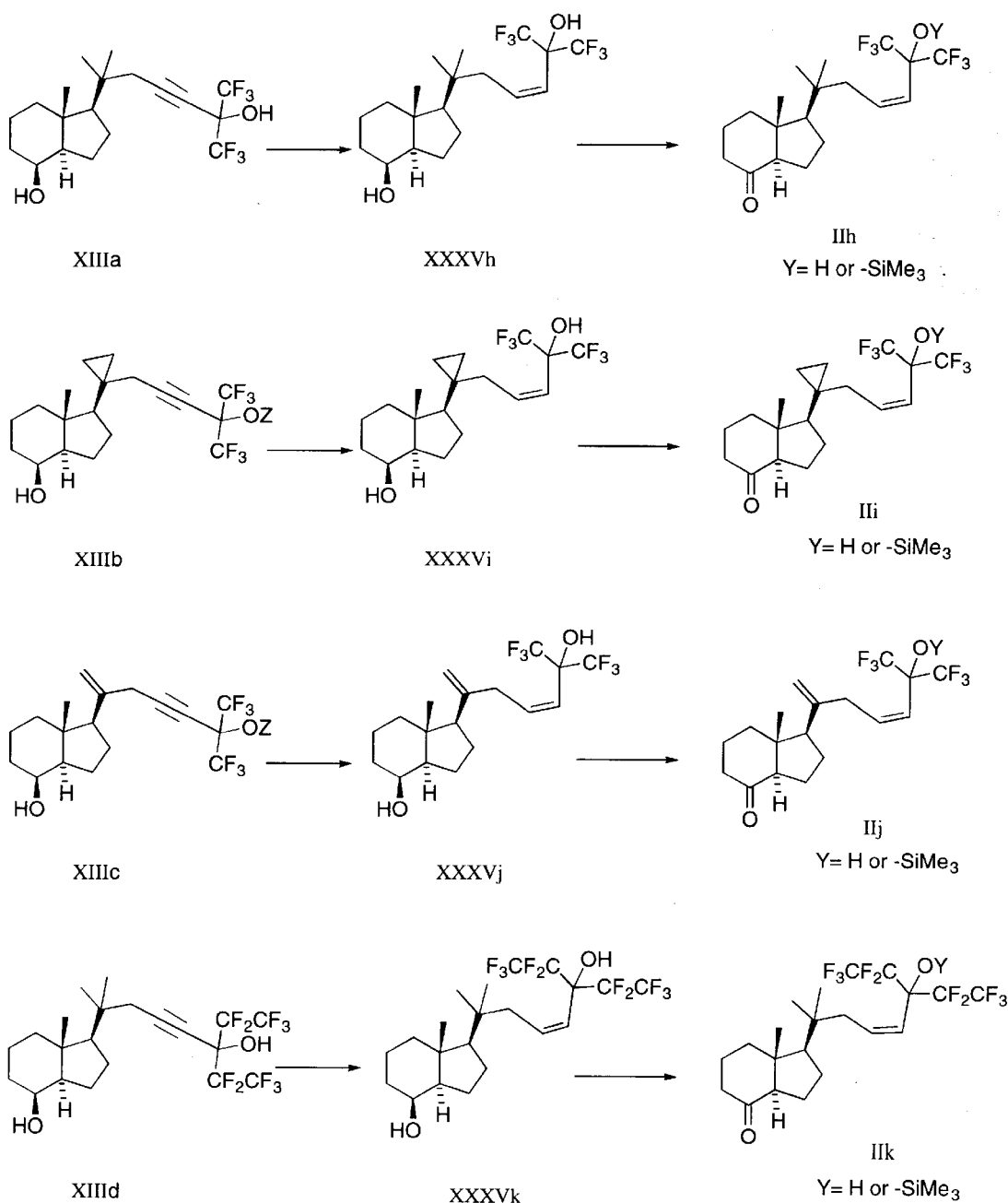
FIGS. 15 and 15a illustrates the synthesis of key intermediates (IIh), (IIi), (IIj), (IIk), (IIl), (IIm) and (IIn).
Figure 15A:
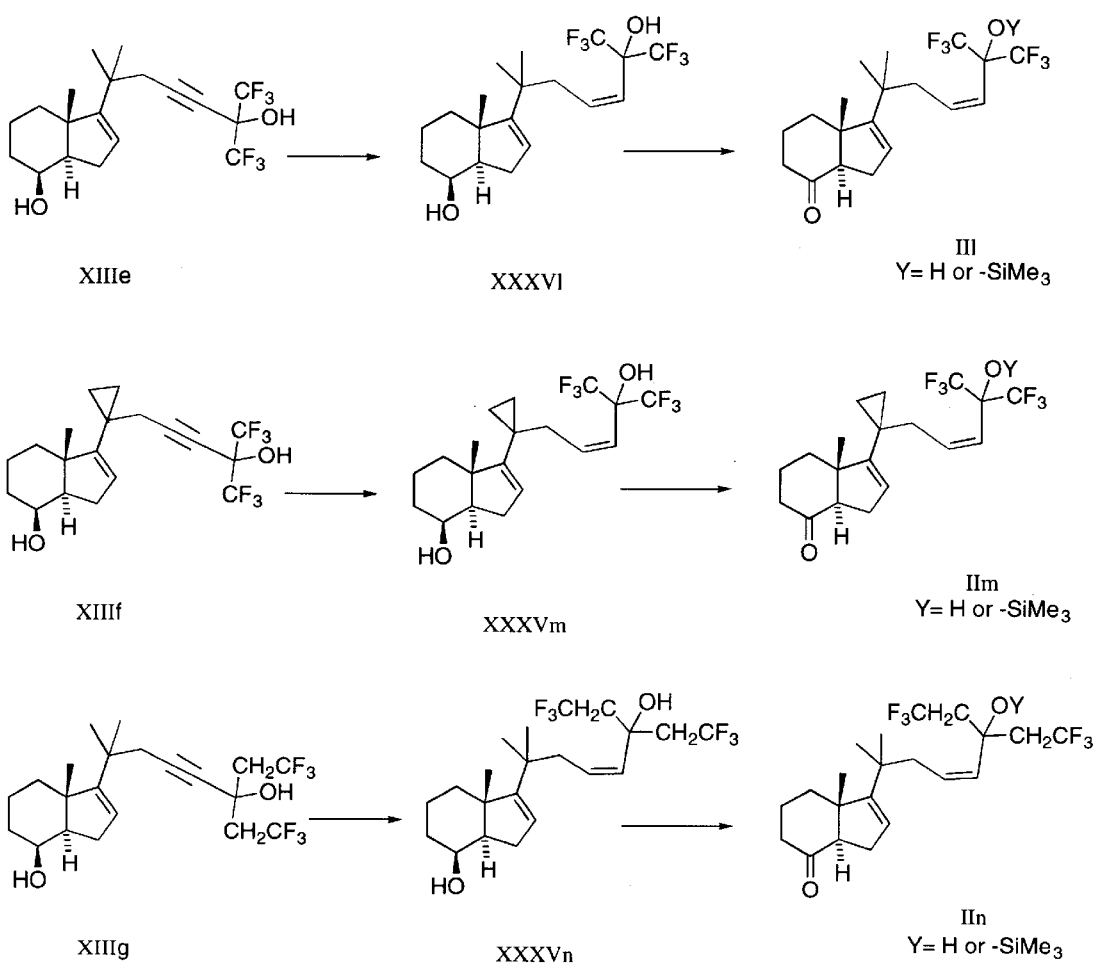
Figure 16:
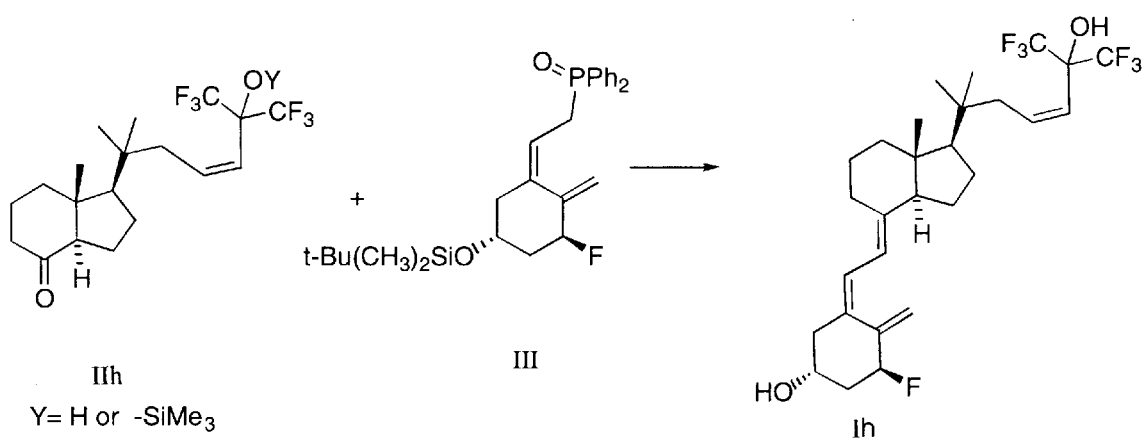
FIG. 16 illustrates the synthesis of the 20-methyl analog (Ih) of 1α-fluoro-25-hydroxy-23Z-ene-26,27-hexafluoro-cholecalciferol.
Figure 17:
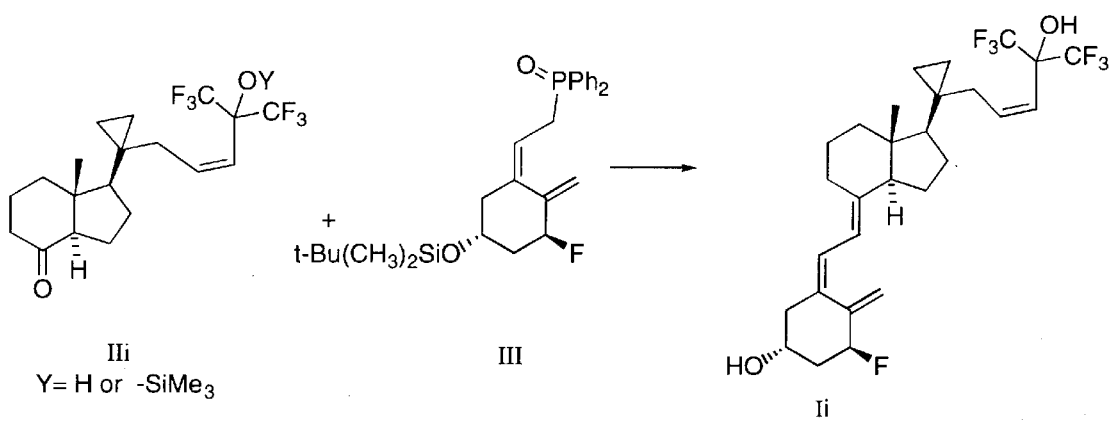
FIG. 17 illustrates the synthesis of the 20-cyclopropyl analog (Ii) of 1α-fluoro-25-hydroxy-23Z-ene-26,27-hexafluoro-cholecalciferol.
Figure 18:
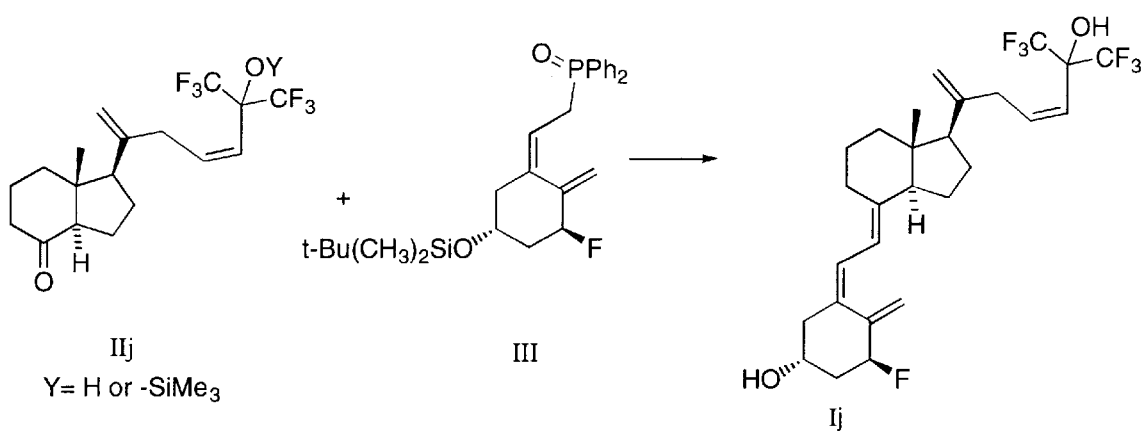
FIG. 18 illustrates the synthesis of the 20-ene-analog (Ij) of 1α-fluoro-25-hydroxy-23Z-ene-26,27-hexafluoro-cholecalciferol.
Figure 19:
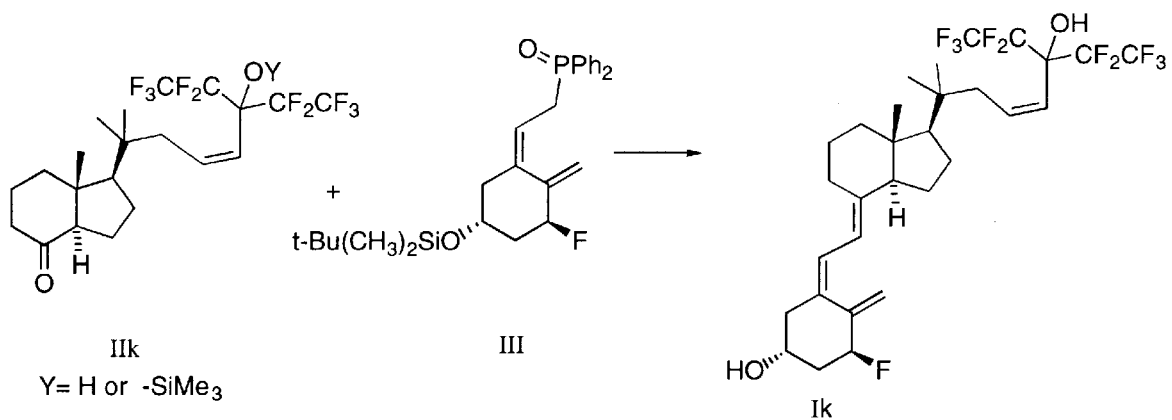
FIG. 19 illustrates the synthesis of the 20-methyl-26,27-bishomo-26,26a,27,27a-decafluoro analog (Ik) of 1α-fluoro-25-hydroxy-23Z-ene-cholecalciferol.

For the synthesis of 23Z-ene vitamin D analogs with various modifications at C-20, the previously cited 23-yne intermediates XIII(*a–g*) may be hydrogenated with Lindlar catalyst to produce 23Z-ene congeners XXXV(*h–m*), from which the corresponding ketones II(*h–m*) where Y is hydrogen are obtained by oxidation as shown in FIGS. 15 and 15a Ketones II(*h–m*) where Y is hydrogen can be converted to the corresponding trimethylsilyl ether derivatives, if desired, as described previously.

h. Synthesis of the 20-methyl analog (I*h*) of 1α-fluoro-25-hydroxy-23Z-ene-26,27-hexafluoro-cholecalciferol is illustrated in FIG. 16, and described in Example 8.

i. Synthesis of the 20-cyclopropyl analog (I*i*) of 1α-fluoro-25-hydroxy-23Z-ene-26,27-hexafluoro-cholecalciferol is illustrated in FIG. 17, and described in Example 9.

j. Synthesis of the 20-ene-analog (I*j*) of 1α-fluoro-25-hydroxy-23Z-ene-26,27-hexafluoro-cholecalciferol is illustrated in FIG. 18, and described in Example 10.

k. Synthesis of the 20-methyl-26,27-bishomo-26,26a,27,27a-decafluoro analog (I*k*) of 1α-fluoro-25-hydroxy-23Z-ene-cholecalciferol is illustrated in FIG. 19, and described in Example 11.

Figure 20:
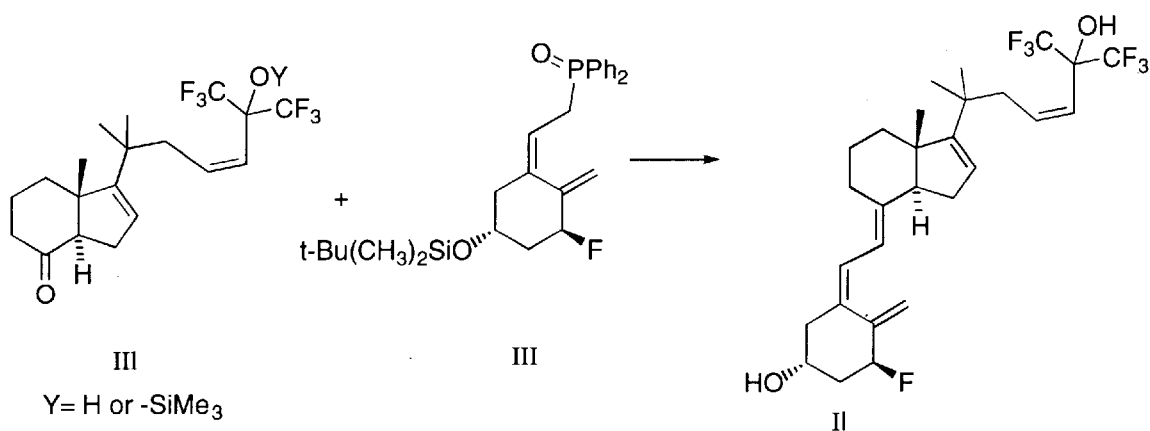
FIG. 20 illustrates the synthesis of the 20-methyl analog (Il) of 1α-fluoro-25-hydroxy-16,23Z-diene-26,27-hexafluoro-cholecalciferol.
Figure 21:
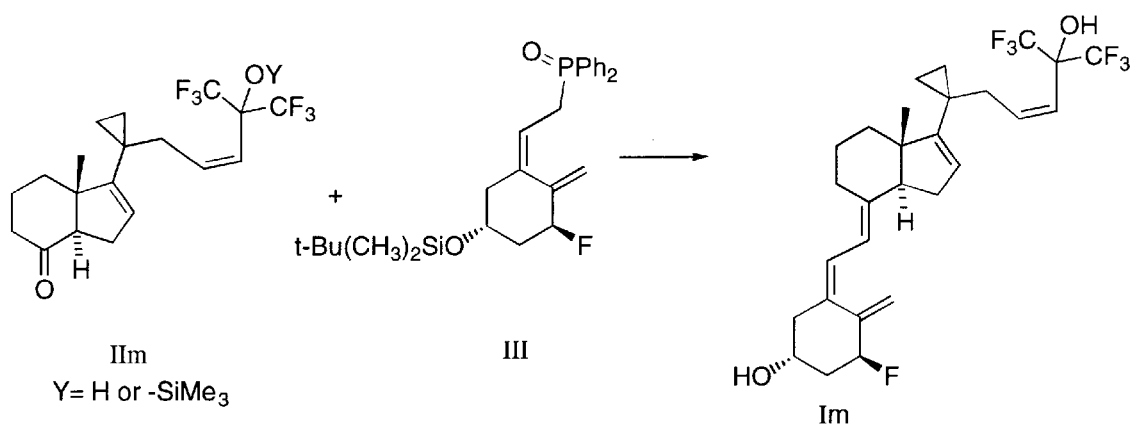
FIG. 21 illustrates the synthesis of the 20-cyclopropyl analog (Im) of 1α-fluoro-25-hydroxy-16,23Z-diene-26,27-hexafluoro-cholecalciferol.
Figure 22:
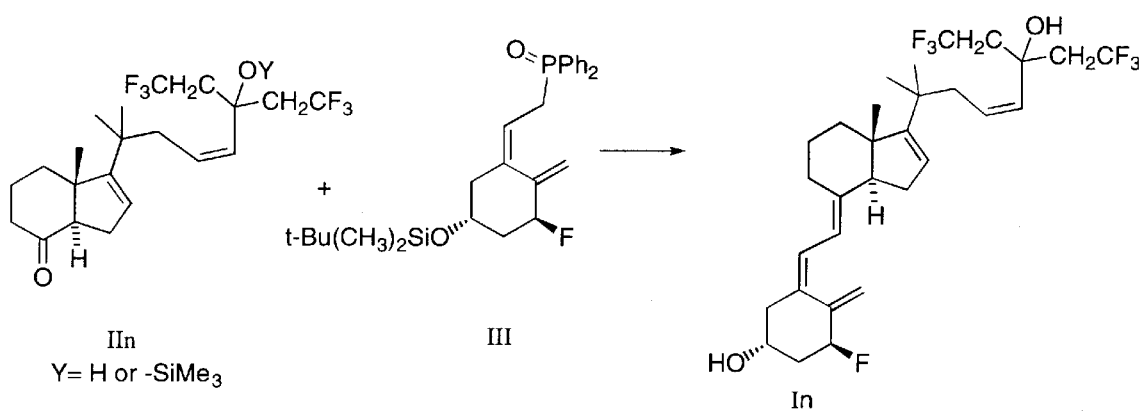
FIG. 22 illustrates the synthesis of the 20-methyl-26,27-bishomo-26a,27a-hexafluoro analog (In) of 1α-fluoro-25-hydroxy-16,23Z-diene-cholecalciferol.

16,23Z-Diene Analogs l. Synthesis of the 20-methyl analog (I*l*) of 1α-fluoro-25-hydroxy-16,23Z-diene-26,27-hexafluoro-cholecalciferol is illustrated in FIG. 20, and described in Example 12.

m. Synthesis of the 20-cyclopropyl analog (I*m*) of 1α-fluoro-25-hydroxy-16,23Z-diene-26,27-hexafluoro-cholecalciferol is illustrated in FIG. 21, and described in Example 13.

n. Synthesis of the 20-methyl-26,27-bishomo-26a,27a-hexafluoro analog (I$n$) of 1α-fluoro-25-hydroxy-16,23Z-diene-cholecalciferol is illustrated in FIG. 22, and described in Example 14.

23E-ene Analogs

Figure 23:
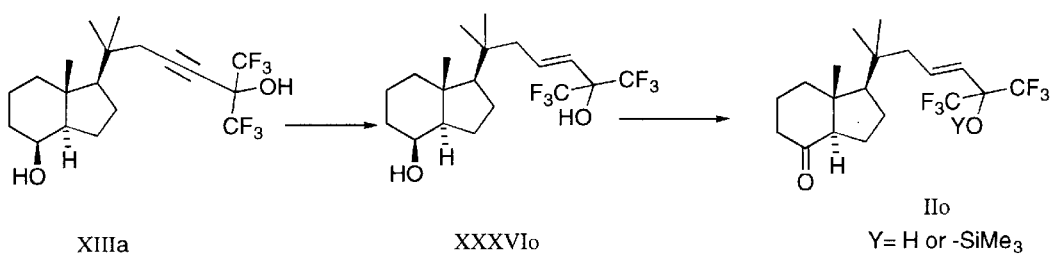
FIGS. 23 and 23a illustrates the synthesis of key intermediates (IIo), (IIp), (IIq), (IIr), (IIs), (IIt) and (IIu).
Figure 23:
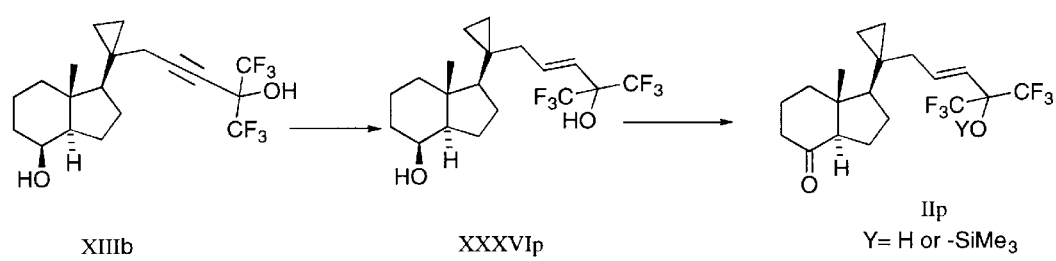
Figure 23:
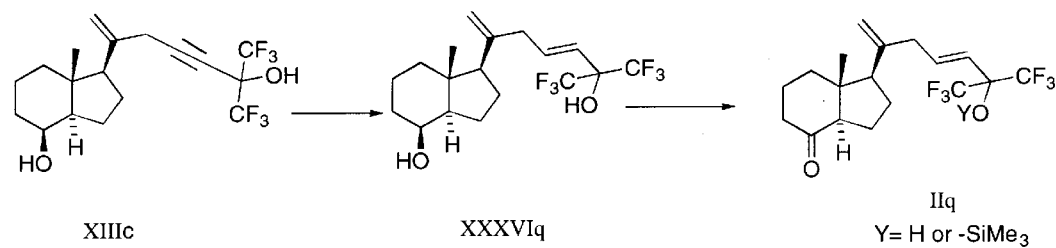
Figure 23:
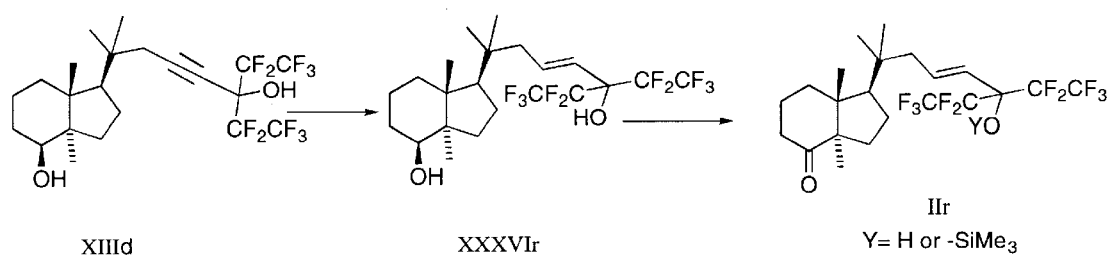
Figure 23A:
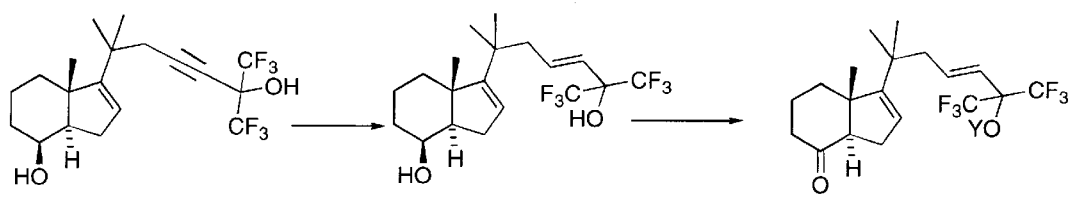
Figure 23A:
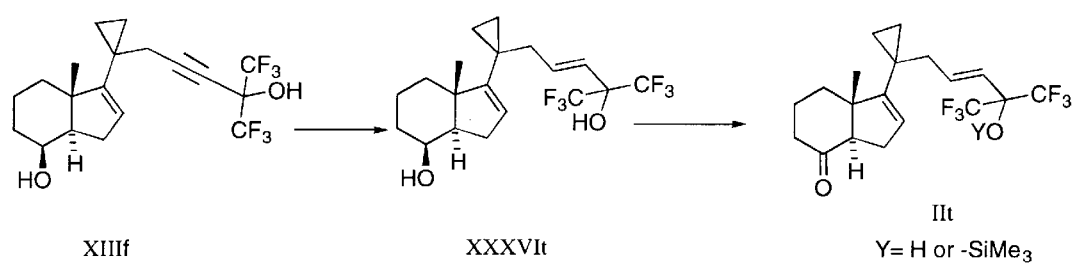
Figure 23A:
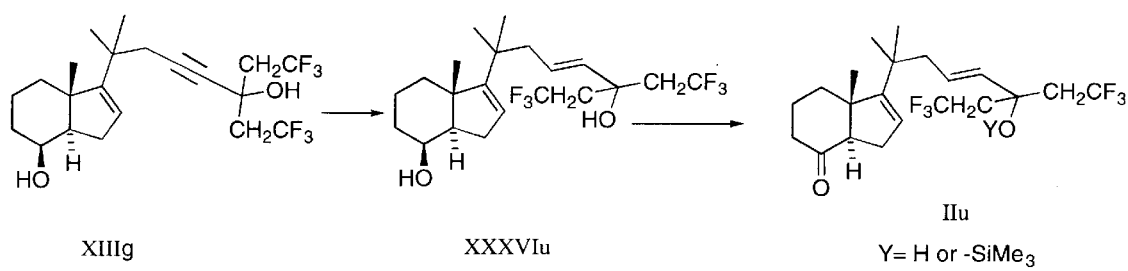
Figure 24:
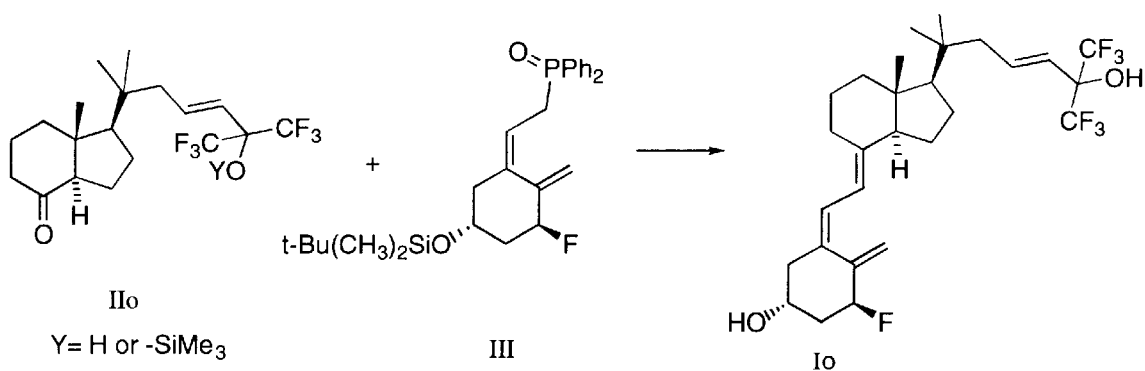
FIG. 24 illustrates the synthesis of the 20-methyl analog (Io) of 1α-fluoro-25-hydroxy-23E-ene-26,27-hexafluoro-cholecalciferol.
Figure 25:
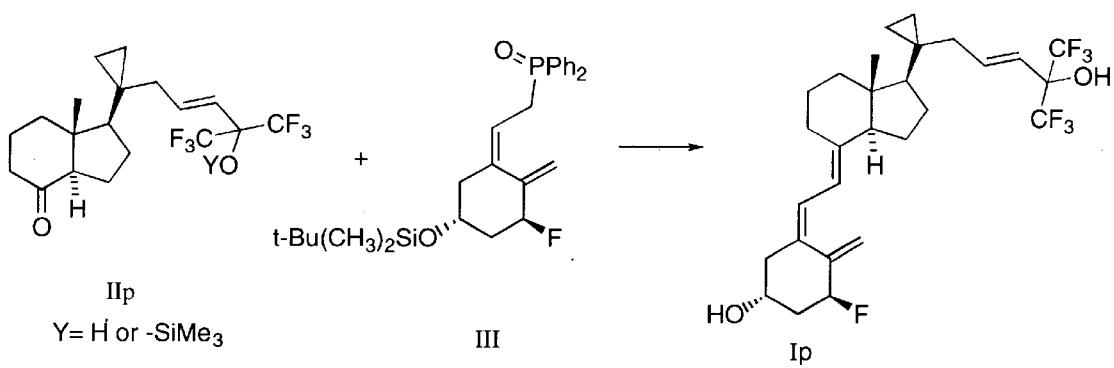
FIG. 25 illustrates the synthesis of the 20-cyclopropyl analog (Ip) of 1α-fluoro-25-hydroxy-23E-ene-26,27-hexafluoro-cholecalciferol.
Figure 26:
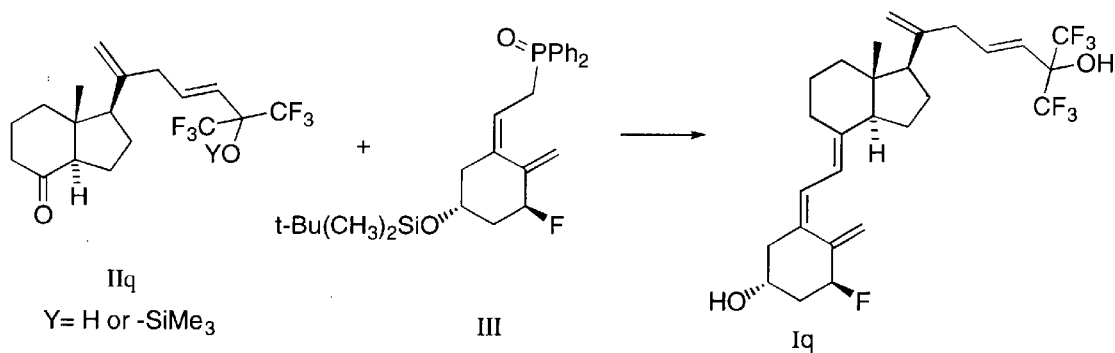
FIG. 26 illustrates the synthesis of the 20-ene analog (Iq) of 1α-fluoro-25-hydroxy-23E-ene-26,27-hexafluoro-cholecalciferol.
Figure 27:
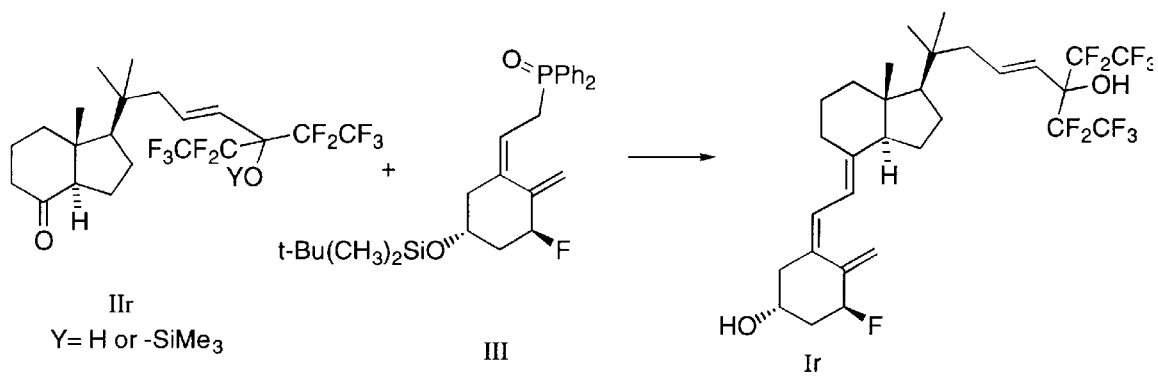
FIG. 27 illustrates the synthesis of the 20-methyl 26,27-bishomo-26,26a,27,27a-decafluoro analog (Ir) of 1α-fluoro-25-hydroxy-23E-ene-cholecalciferol.

For the synthesis of 23E-ene vitamin D analogs with various modifications at C-20, the previously cited 23-yne intermediates XIII($a$–$g$) are reduced with lithium aluminum hydride in the presence of sodium methoxide to produce 23E-ene congeners XXXVI($o$–$u$), from which the corresponding ketones II($o$–$u$) where Y is hydrogen are obtained by oxidation as shown in FIGS. 23 and 23$a$. Ketones II($h$–$m$) where Y is hydrogen can be converted to the corresponding trimethylsilyl ether derivatives, if desired, as described above. Anal. data for intermediate II$p$ (Y=hydrogen): mp 79°–80° C.; $[\alpha]_D^{25}$=+6.90° (c 1.00, EtOH); MS m/z 398 (M$^+$, 20).

o. Synthesis of the 20-methyl analog (I$o$) of 1α-fluoro-25-hydroxy-23E-ene-26,27-hexafluoro-cholecalciferol is illustrated in FIG. 24, and described in Example 15.

p. Synthesis of the 20-cyclopropyl analog (I$p$) of 1α-fluoro-25-hydroxy-23E-ene-26,27-hexafluoro-cholecalciferol is illustrated in FIG. 25, and described in Example 16.

q. Synthesis of the 20-ene analog (I$q$) of 1l-fluoro-25-hydroxy-23E-ene-26,27 hexafluoro-cholecalciferol is illustrated in FIG. 26, and described in Example 17.

r. Synthesis of the 20-methyl 26,27-bishomo-26,26a,27,27a-decafluoro analog (I$r$) of 1α-fluoro-25-hydroxy-23E-ene-cholecalciferol is illustrated in FIG. 27, and described in Example 18.

Figure 28:
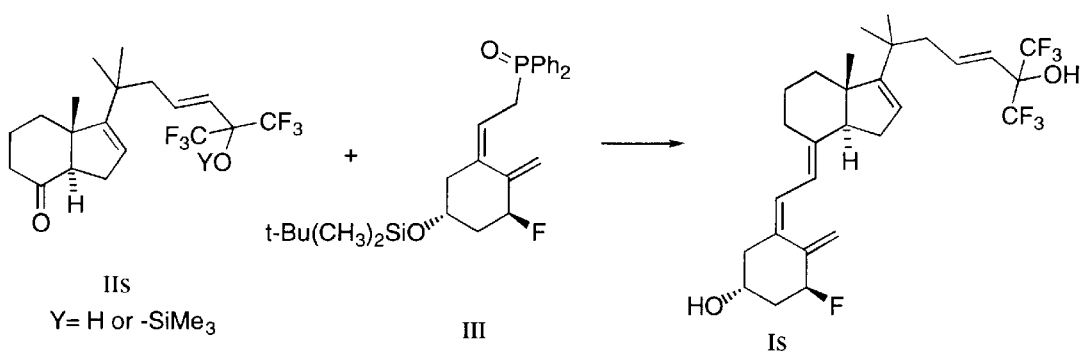
FIG. 28 illustrates the synthesis of the 20-methyl analog (Is) of 1α-fluoro-25-hydroxy-16,23E-diene-26,27-hexafluoro-cholecalciferol.
Figure 29:
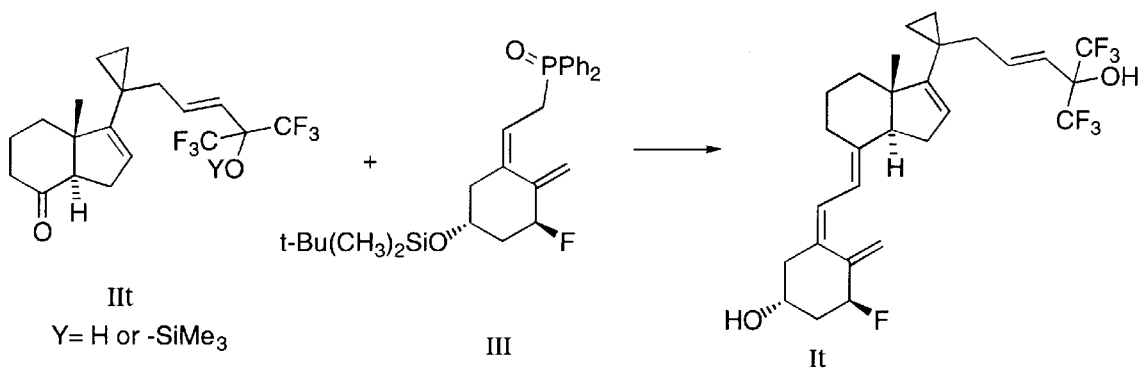
FIG. 29 illustrates the synthesis of the 20-cyclopropyl analog (It) of 1α-fluoro-25-hydroxy-16,23E-diene-26,27-hexafluoro-cholecalciferol.
Figure 30:
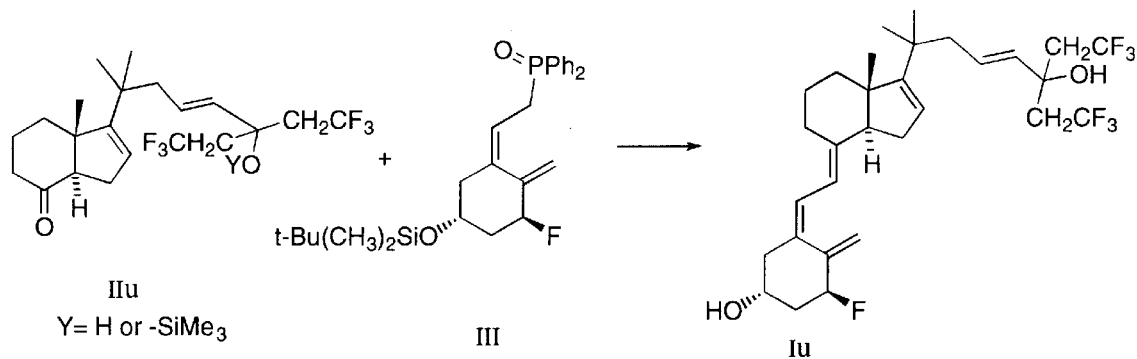
FIG. 30 illustrates the synthesis of the 20-methyl-26,27-bishomo-26a,27a-hexafluoro analog (Iu) of 1α-fluoro-25-hydroxy-16,23E-diene-cholecalciferol.

16,23E-Diene Analogs s. Synthesis of the 20-methyl analog (I$s$) of 1α-fluoro-25-hydroxy-16,23E-diene-26,27-hexafluoro-cholecalciferol is illustrated in FIG. 28, and described in Example 19.

t. Synthesis of the 20-cyclopropyl analog (I$t$) of 1α-fluoro-25-hydroxy-16,23E-diene-26,27-hexafluoro-cholecalciferol is illustrated in FIG. 29, and described in Example 20.

u. Synthesis of the 20-methyl-26,27-bishomo-26a,27a-hexafluoro analog (I$u$) of 1α-fluoro-25-hydroxy-16,23E-diene-cholecalciferol is illustrated in FIG. 30, and described in Example 21.

Figure 31:
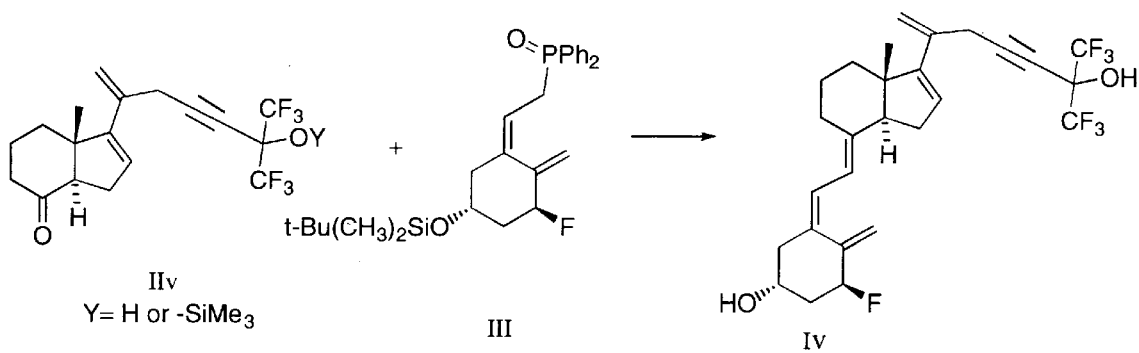
FIGS. 31, 32 & 32a illustrate the synthesis of the 20-ene analog (Iv) of 1α-fluoro-25-hydroxy-16-ene-23-yne-26,27-hexafluoro-cholecalciferol and intermediates (IIv) and (XXXIXv) used in the preparation of (Iv), respectively.

16,20-Diene-23-yne Analogs v. Synthesis of the 20-ene analog (I$v$) of 1α-fluoro-25-hydroxy-16-ene-23-yne-26,27-hexafluoro-cholecalciferol is illustrated in FIG. 31, and described in Example 22.

Figure 32:
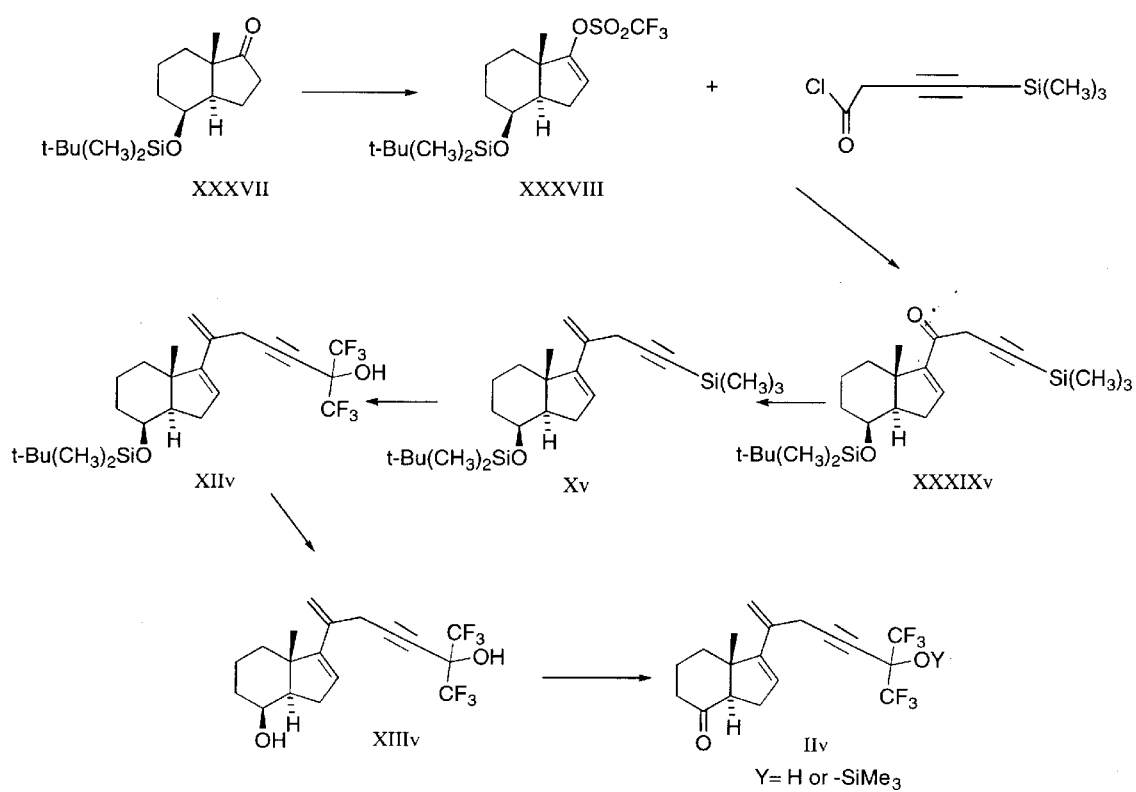
Figure 32A:
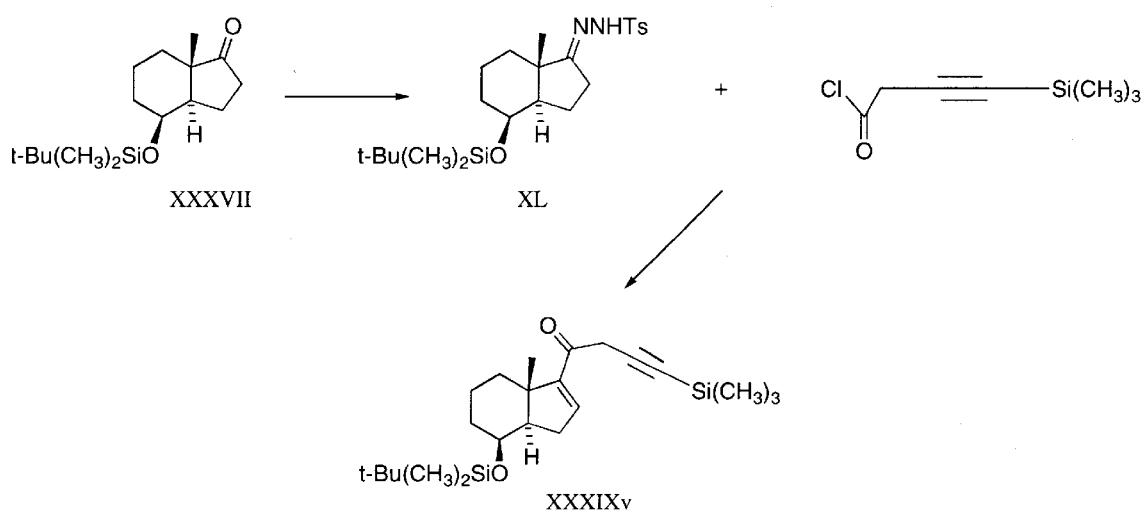

The key intermediate II$v$ where Y is hydrogen or -SiMe$_3$ can be prepared according to the synthesis outlined in FIG. 32.

This synthesis starts from the known ketone XXXVII and constitutes a novel entry into the 16-ene class of vitamin D analogs. The side chain is attached by a palladium catalyzed coupling of the enol triflate XXXVIII with the trimethylsilylbutynoic acid chloride to give the ketone XXXIX$v$, from which the side chain of II$v$ is completed by standard methods. An alternative for the conversion of XXXVII to the ketone is the use of Shapiro reaction shown in FIG. 32$a$.

Figure 33:
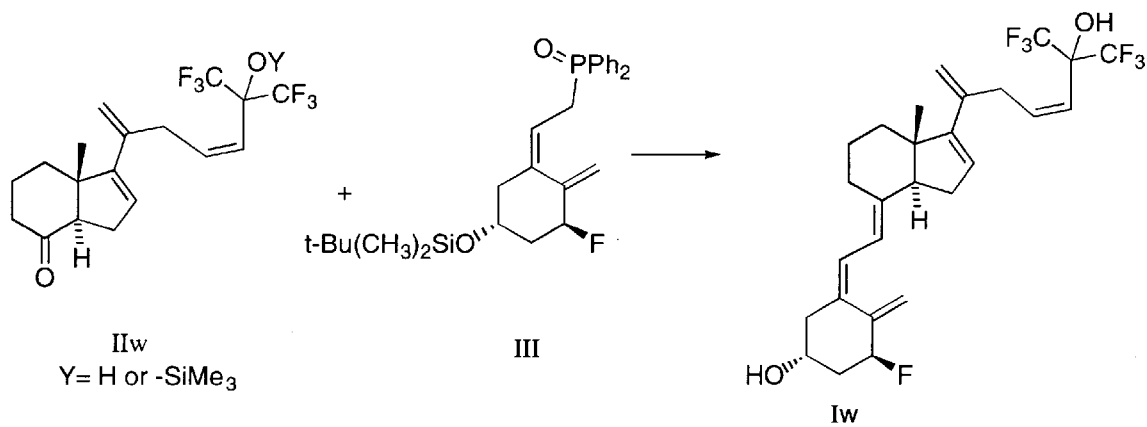
FIGS. 33 & 34 illustrate the synthesis of the 20-ene analog (Iw) of 1α-fluoro-25-hydroxy-16,23Z-diene-26,27-hexafluoro-cholecalciferol and intermediates (IIw) used in the preparation of (Iw), respectively.

16,20,23Z-Triene Analogs w. Synthesis of the 20-ene analog (I$w$) of 1α-fluoro-25-hydroxy-16,23Z-diene-26,27-hexafluoro-cholecalciferol is illustrated in FIG. 33, and described in Example 23.

Figure 34:
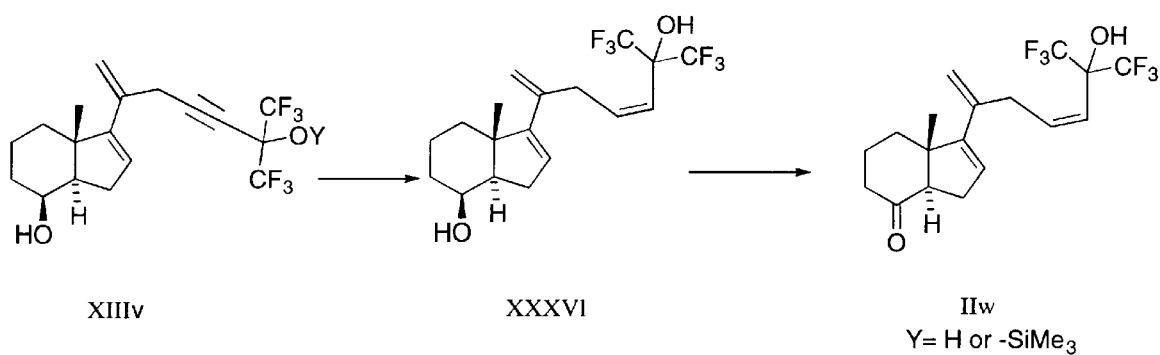

The key intermediate II$w$ where Y is hydrogen or -SiMe$_3$ can be prepared according to FIG. 34 starting from the previously cited compound XIII$v$ (FIG. 32) by hydrogenation using the Lindlar catalyst, followed by oxidation and silylation.

Figure 35:
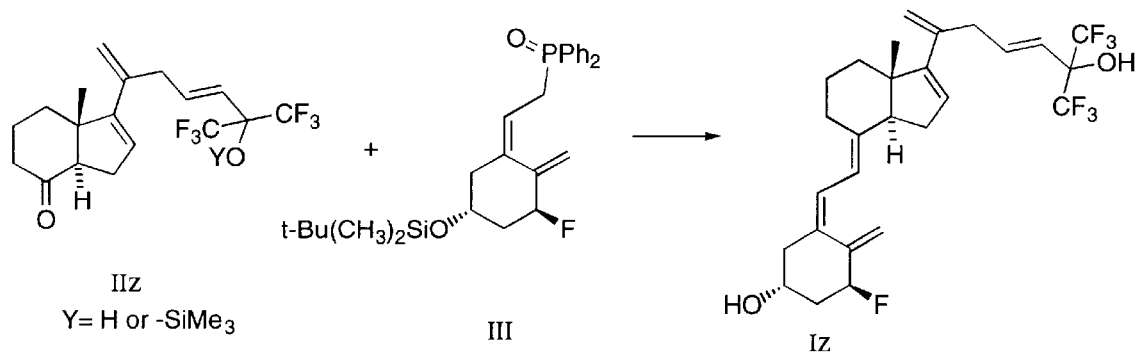
FIGS. 35 & 36 illustrate the synthesis of the 20-ene analog (Iz) of 1α-fluoro-25-hydroxy-16,23Z-diene-26,27-hexafluoro-cholecalciferol and intermediates (IIz) used in the preparation of (Iz), respectively.

16,20,23E-Triene Analogs z. Synthesis of the 20-ene analog (I$z$) of 1α-fluoro-25-hydroxy-16,23E-diene-26,27-hexafluoro-cholecalciferol is illustrated in FIG. 35, and described in Example 24.

Figure 36:
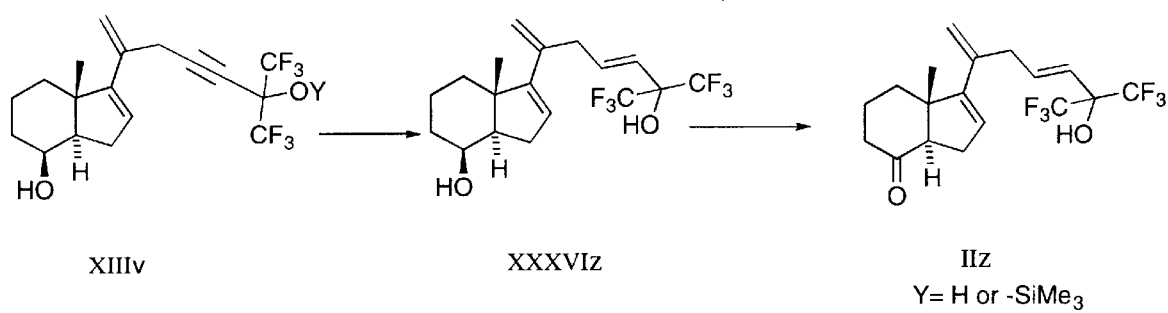

In this case the key intermediate II$z$ where Y is hydrogen can be prepared according to FIG. 36 starting from XIII$v$ (Scheme 32) by reduction with lithium aluminum hydride in the presence of sodium methoxide, followed by oxidation. II$z$ where Y is hydrogen can be converted to the corresponding trimethylsilyl ether derivative, if desired, as described previously.

1α-Fluoro-19-Nor Analogs

Figure 37:
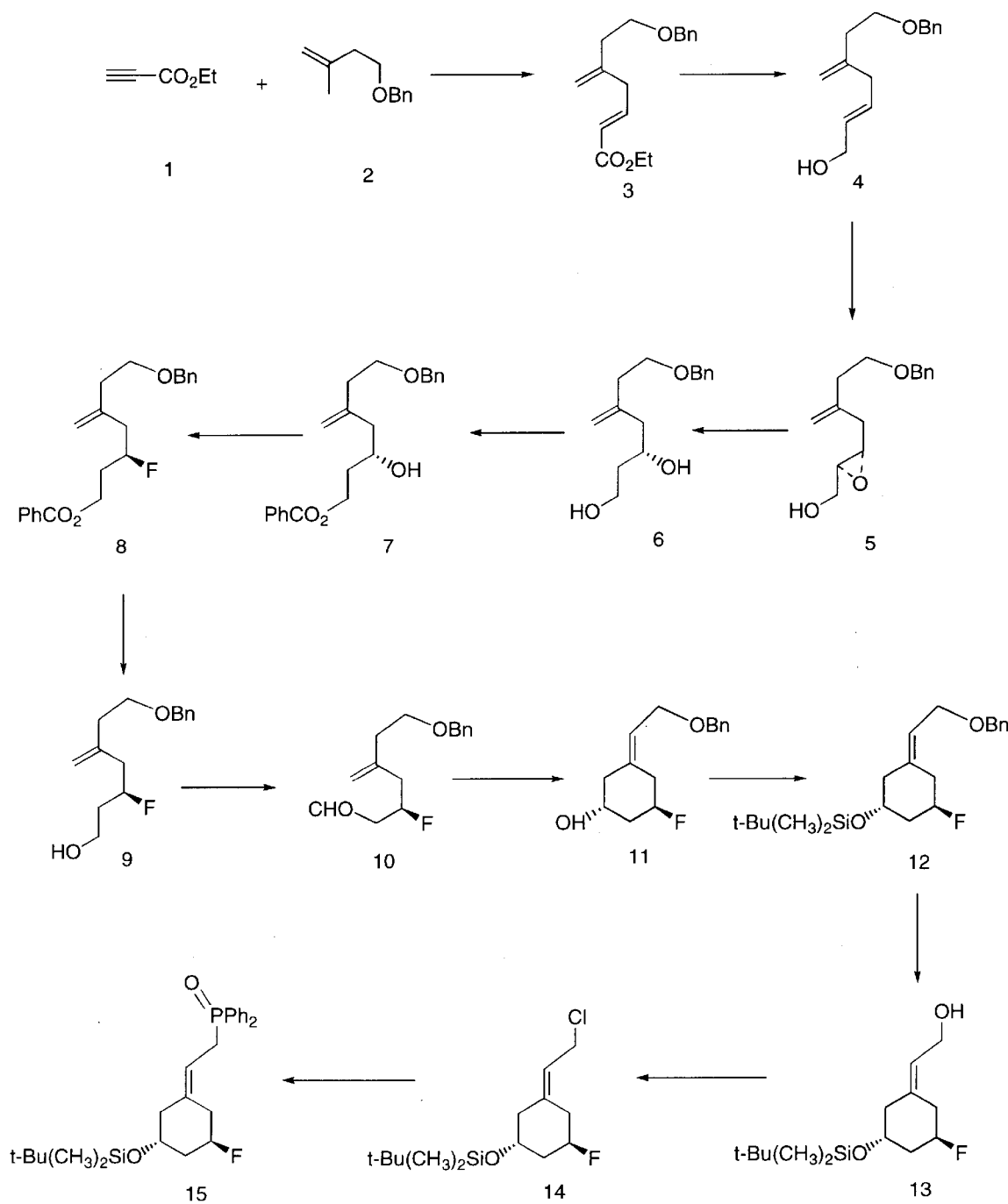
FIG. 37 illustrates the synthesis of the precursor (3R-(3α,5β,Z)]-2 [2-[3-fluoro-5-[[(1,1-dimethylethyl)-dimethylsilyl]oxy]cyclohexylidene]ethyl] diphenyl phosphine oxide (15) used in the synthesis of 1α-fluoro-19-nor Vitamin D.

The precursor (3R-(3α,5β,Z)]-2[2-[3-fluoro-5-[[(1,1-dimethylethyl)dimethylsilyl]oxy]cyclo-hexylidene]ethyl] diphenyl phosphine oxide (15) needed for the synthesis of 1α-fluoro-19-nor Vitamin D analogs can be prepared by the synthesis outlined as follows and illustrated in FIG. 37. Synthesis of a specific 1α-fluoro-19-nor analog is described in Example 25.

The diene-ester (3) is obtainable by an ene reaction starting from ethyl propionate (1) and 3-methyl-but-3-en-1-ol benzyl ether (2) catalyzed with ethyl aluminum dichloride as a Lewis acid. The reduction of the ester (3) to the allylic alcohol (4) proceeds with diisobutyl aluminum hydride in tetrahydrofuran solution. The formation of the epoxide (5) from the allylic alcohol (4) results from a Sharpless epoxidation using D-(-)-diethyl tartrate, titanium(IV)-isopropoxide and tert-butyl hydroperoxide in the presence of activated 4A sieves in dichloromethane solution.

The reduction of the epoxide (5) to the 1,3-diol (6) can be effected using Red-Al™ (Aldrich) as reducing agent. The diol (6) can be selectively converted to the mono-benzoate (7) with benzoyl chloride in the presence of pyridine in dichloromethane solution. The replacement of the hydroxy group of (7) with fluorine to give the fluoro-ester (8) with an inversion of configuration is expected from the reaction of (7) with diethylaminosulfur trifluoride (DAST) at −92° C. The fluoro-ester (8) can be hydrolyzed to the fluoro-alcohol (9) with lithium methoxide in methanol. The oxidation of the fluoro-alcohol (9) to the fluoro-aldehyde (10) can be achieved by reaction with oxalyl chloride, dimethyl sulfoxide and triethylamine at −70° C. to room temperature.

The cyclization of the fluoro-aldehyde (10) to the fluorocyclohexanol (11), an ene reaction, can be promoted with a reagent obtained from 2,6-di-tert-butyl-4-methyl-phenol and trimethyl aluminum as a Lewis acid at −78° in dichloromethane solution. The newly formed hydroxy group of (11) is protected as tert-butyl dimethylsilyl (12) by a reaction of (11) with imidazole and tert-butyl-dimethylsilyl chloride in dimethylformamide as a solvent at room temperature. The removal of the benzyl protecting group of (12) to give the allylic alcohol (13) is achievable by reduction with lithium di-tert-butylbiphenylide in tetrahydrofuran solution at −78°. The conversion of the allylic alcohol (13) to the diphenyl phosphate oxide (15) can be done using known methods.

As described above, also provided are intermediates for synthesizing compounds of Formula (I). These intermediates are compounds of Formula (II)

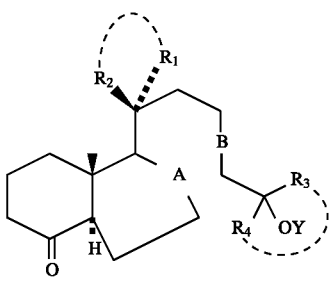

(II)

wherein:

$R_1$ and $R_2$ are
(a) both methyl,
(b) together with the carbon to which they are attached form a cyclopropane ring, or
(c) form a =$CH_2$;

$R_3$ and $R_4$ are, independently of each other, a ($C_1$–$C_4$) alkyl or fluoroalkyl, or $R_3$ and $R_4$ together with C-25 form a ($C_3$–$C_9$) cycloalkyl or cyclofluoroalkyl;

A is a single bond or a double bond;

B is a double bond or a triple bond; and

Y is H or $OSiMe_3$.

Utility

The compounds of this invention are useful for the prevention and treatment of a variety of mammalian conditions manifested by loss of bone mass. In particular, the compounds of this invention are indicated for the prophylaxis and therapeutic treatment of osteoporosis and osteopenia in mammals without inducing hypercalciuria, hypercalcemia, or nephrotoxicity. As used herein, "hypercalciuria" is excessive calcium in the urine, in humans corresponding to an excretion of greater than 4 mg/kg/day. This often results in nephrolithiasis (renal calculi). "Hypercalcemia" is an excessive concentration of calcium in the serum; in humans (and rats) this corresponds to greater than about 10.5 mg/dl. "Intolerable hypercalcemia", usually occurring at serum calcium concentrations greater than about 12 mg/dl, is associated with emotional lability, confusion, delirium, psychosis, stupor, and coma.

The compounds of this invention are expected to be useful in the treatment of Type I (postmenopausal), Type II (senile), and Type III (iatrogenic) osteoporosis, including that associated with immunosuppressive drugs used in organ transplantation, as well in the treatment of osteodystrophy due to renal dialysis and hyperparathyroidism.

Administration & Pharmaceutical compositions

In general, the compound of this invention may be administered in amounts between about 0.0002 and 0.5 μg compound/kg body weight per day, preferably from about 0.001 to about 0.1 μg/kg body weight per day, most preferably from about 0.002 to about 0.02 μg/kg body weight per day. For a 50 kg human subject, the daily dose of active ingredient may be from about 0.01 to about 25 μgs, preferably from about 0.05 to about 10 μgs most preferably from about 0.1 μg to about 1μg per day. In other mammals, such as horses, dogs, and cattle, other doses may be required. This dosage may be delivered in a conventional pharmaceutical composition by a single administration, by multiple applications, or via controlled release, as needed to achieve the most effective results, preferably once or twice daily by mouth. In certain situations, alternate day dosing may prove adequate to achieve the desired therapeutic response.

The selection of the exact dose and composition and the most appropriate delivery regimen will be influenced by, inter alia, the pharmacological properties of the formulation, the nature and severity of the condition being treated, and the physical condition and mental acuity of the recipient. In the treatment of corticosteroid induced osteopenia, it is expected that the requisite dose will be greater for higher doses of corticosteroids.

Representative delivery regimens include oral, parenteral (including subcutaneous, intramuscular and intravenous), rectal, buccal (including sublingual), pulmonary, transdermal, and intranasal, most preferably oral.

A further aspect of the present invention relates to pharmaceutical compositions comprising as an active ingredient a compound of the present invention, in admixture with a pharmaceutically acceptable, non-toxic carrier. As mentioned above, such compositions may be prepared for parenteral (subcutaneous, intramuscular or intravenous) administration, particularly in the form of liquid solutions or suspensions; for oral or buccal administration, particularly in the form of tablets or capsules; for pulmonary or intranasal administration, particularly in the form of powders, nasal drops or aerosols; and for rectal or transdermal administration.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like. Formulations for nasal administration may be solid and may contain excipients, for example, lactose or dextran, or may be aqueous or oily solutions for use in the form of nasal drops or metered spray. For buccal administration typical excipients include sugars, calcium stearate, magnesium stearate, pregelatinated starch, and the like.

Orally administrable compositions may comprise one or more physiologically compatible carriers and/or excipients and may be in solid or liquid form, including, for example, tablets, coated tablets, capsules, lozenges, aqueous or oily suspensions, solutions, emulsions, elixirs, and powders suitable for reconstitution with water or another suitable liquid vehicle before use. Tablets and capsules may be prepared with binding agents, for example, syrup, acacia, gelatin, sorbitol, tragacanth, or poly-vinylpyrollidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethylcellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Preferred solid oral dosage forms include tablets, two-piece hard shell capsules and soft elastic gelatin (SEG) capsules. SEG capsules are of particular interest because they provide distinct advantages over the other two forms (see Seager, H., "Soft gelatin capsules: a solution to many tableting problems"; Pharmaceutical Technology, 9, (1985). Some of the advantages of using SEG capsules are: a)

dose-content uniformity is optimized in SEG capsules because the drug is dissolved or dispersed in a liquid that can be dosed into the capsules accurately b) drugs formulated as SEG capsules show good bioavailability because the drug is dissolved, solubilized or dispersed in an aqueous-miscible or oily liquid and therefore when released in the body the solutions dissolve or are emulsified to produce drug dispersions of high surface area and c) degradation of drugs that are sensitive to oxidation during long-term storage is prevented because the dry shell of soft gelatin provides a barrier against the diffusion of oxygen.

The dry shell formulation typically comprises of about 40% to 60% concentration of gelatin, about a 20% to 30% concentration of plasticizer (such as glycerin, sorbitol or propylene glycol) and about a 30 to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

Also provided are methods of treating osteoporosis and other bone related diseases, particularly those related to the loss of bone mass, via adminstration of a compound of Formula (I),

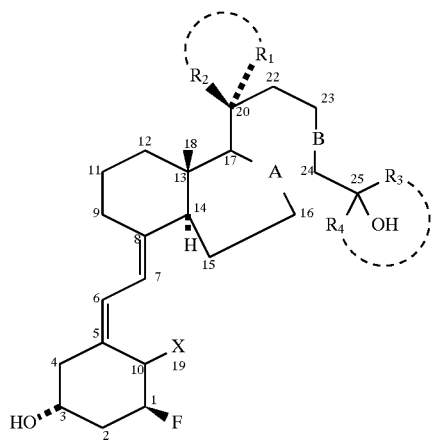

wherein:
X is hydrogen or $=CH_2$;
X is hydrogen or $=CH_2$;
$R_1$ and $R_2$ are, independently of each other, hydrogen or $(C_1-C_4)$ alkyl or fluoroalkyl, or $R_1$ and $R_2$ together with C-20 form a $(C_3-C_6)$ cycloalkyl or cyclofluoroalkyl, or one of $R_1$ and $R_2$ together form $=CH_2$;
$R_3$ and $R_4$ are, independently of each other, a $(C_1-C_4)$ alkyl or fluoroalkyl, or $R_3$ and $R_4$ together with C-25 form a $(C_3-C_9)$ cycloalkyl or cyclofluoroalkyl;
A is a single bond or a double bond; and
B is a double bond or a triple bond;
except that where $R_3$ and $R_4$ are each $CF_3$ and A is a double bond and B is a triple bond and $R_2$ is hydrogen, then $R_1$ cannot be $CH_3$.

Pharmaceutical compositions, dosages and delivery regimens for these methods of treatment are as described earlier. The methods are of particular utility in treating osteoporosis in a human female.

Preferred embodiments of the treatment method are administration of a compound of Formula I, wherein:

X is $=CH_2$;
one of $R_1$ and $R_2$ is hydrogen and the other is $CH_3$;
$R_3$ and $R_4$ are each $C_2H_5$;
A is a double bond; and
B is a trans double bond.

Pharmaceutical compositions, dosages and delivery regimens for these methods of treatment are as described earlier. The methods are of particular utility in treating osteoporosis in a human female.

EXAMPLES

The following examples are given to enable those skilled in the art to more clearly understand and to practice the present invention. They should not be considered as limiting the scope of the invention, but merely as being illustrative and representative thereof.

It should be noted that although the following synthetic examples specifically describe the preparations of a compound of Formula (I) from intermediate II where Y is hydrogen, that compound (I) can also be prepared from the corresponding silylated derivative of intermediate II (Y=SiMe$_3$) under the same reaction conditions.

Example 1

1α-Fluoro-25-hydroxy-23-yne-26,27-hexafluoro-20-methyl-cholecalciferol

The title compound can be prepared by the following procedure:

To a solution of 1.5 mmole (3S-(3α,5β,Z)]-2-[2-[2-methylene-3-fluoro-5-[[(1,1-dimethylethyl)dimethylsilyl]oxy] cyclohexylidene]ethyl]diphenyl phosphine oxide (III) in 9 ml anhydrous tetrahydrofuran at −78° C. is added 1.5 mmole of 1.6M n-butyllithium in hexane dropwise in an argon atmosphere. After stirring for 5 minutes, a solution of 0.6 mmole 3aR-(3aα,7aβ)-1,2,3,3a,5,6,7,7a-octahydro-7a-methyl-1-[6,6,6-trifluoro-5-hydroxy-5-trifluoromethyl-1,1-dimethyl-3-hexynyl]-4H-inden-4-one (IIa) in 4 ml of anhydrous tetrahydrofuran is added dropwise over a 10 min period. The reaction mixture is then stirred at −78° C. for 2 hrs., quenched with 2N Rochelle salt and warmed up to room temperature. The isolation of the silylated title compound can be done by extraction with ethyl acetate and purification by FLASH chromatography.

Removal of the silyl protecting group can be performed by treating a solution of the silylated title compound in 4 ml of anhydrous tetrahydrofuran with 1.25 mmole of 1M solution of tetrabutylammonium fluoride in tetrahydrofuran under argon and stirring at room temperature for 18 hrs. This reaction mixture is quenched with water and the resulting title compound is isolated by extraction with ethyl acetate and purification by FLASH chromatography.

Example 2

1α-Fluoro-25-hydroxy-23-yne-26,27-hexafluoro-20,21,28-cyclopropyl-cholecalciferol The title compound can be prepared by the following procedure:

To a solution of 1.5 mmole (3S-(3α,5β,Z)]-2-[2-[2-methylene-3-fluoro-5-[[(1,1-dimethylethyl)dimethylsilyl]oxy] cyclohexylidene]ethyl]diphenyl phosphine oxide (III) in 9 ml anhydrous tetrahydrofuran at −78° C. is added 1.5 mmole of 1.6M n-butyllithium in hexane dropwise in an argon atmosphere. After stirring for 5 minutes, a solution of 0.6 mmole 3aR-(3aα,7aβ)-1,2,3,3a,5,6,7,7a-octahydro-7a-methyl-1-[8,8,8-trifluoro-7-hydroxy-7-trifluoromethyl-1,3-cyclo-5-octynyl]-4H-inden-4-one (IIb) in 4 ml of anhydrous tetrahydrofuran is added dropwise over a 10 min period. The reaction mixture is then stirred at −78° C. for 2 hrs., quenched with 2N Rochelle salt and warmed up to room temperature. The isolation of the silylated title compound can be done by extraction with ethyl acetate and purification by FLASH chromatography.

Removal of the silyl protecting group can be performed by treating a solution of the silylated title compound in 4 ml of anhydrous tetrahydrofuran with 1.25 mmole of 1M solution of tetrabutylammonium fluoride in tetrahydrofuran under argon and stirring at room temperature for 18 hrs. This reaction mixture is quenched with water and the resulting title compound is isolated by extraction with ethyl acetate and purification by FLASH chromatography.

Example 3

1α-Fluoro-25-hydroxy-20-ene-23-yne-26,27-hexafluoro-cholecalciferol

The title compound can be prepared by the following procedure:

To a solution of 1.5 mmole (3S-(3α,5β,Z)]-2-[2-[2-2-methylene-3-fluoro-5-[[(1,1-dimethylethyl)dimethylsilyl] oxy] cyclohexylidene]ethyl]diphenyl phosphine oxide (III) in 9 ml anhydrous tetrahydrofuran at −78° C. is added 1.5 mmole of 1.6M n-butyllithium in hexane dropwise in an argon atmosphere. After stirring for 5 minutes, a solution of 0.6 mmole 3aR-(3aα,7aβ)-1,2,3,3a,5,6,7,7a-octahydro-7a-methyl-1-[6,6,6-trifluoro-5-hydroxy-5-trifluoromethyl-1-methylene-3-hexynyl]-4H-inden-4-one (IIc) in 4 ml of anhydrous tetrahydrofuran is added dropwise over a 10 min period. The reaction mixture is then stirred at −78° C. for 2 hrs., quenched with 2N Rochelle salt and warmed up to room temperature. The isolation of the silylated title compound can be done by extraction with ethyl acetate and purification by FLASH chromatography.

Removal of the silyl protecting group can be performed by treating a solution of the silylated title compound in 4 ml of anhydrous tetrahydrofuran with 1.25 mmole of 1M solution of tetrabutylammonium fluoride in tetrahydrofuran under argon and stirring at room temperature for 18 hrs. The reaction mixture is quenched with water and the resulting title compound is isolated by extraction with ethyl acetate and purification by FLASH chromatography.

Example 4

1α-Fluoro-25-hydroxy-23-yne-20-methyl-26,27-bishomo-26,26a,27,27a-decafluoro-cholecalciferol The title compound can be prepared by the following procedure:

To a solution of 1.5 mmole (3S-(3α,5β,Z)]-2-[2-[2-methylene-3-fluoro-5-[[( 1,1-dimethylethyl)dimethylsilyl] oxy]-cyclohexylidene]ethyl]diphenyl phosphine oxide (III) in 9 ml anhydrous tetrahydrofuran at −78° C. is added 1.5 mmole of 1.6M n-butyllithium in hexane dropwise in an argon atmosphere. After stirring for 5 minutes, a solution of 0.6 mmole 3aR-(3aα,7aβ)-1,2,3,3a,5,6,7,7a-octahydro-7a-methyl-1-[6,6,7,7,7-pentafluoro-5-hydroxy-5-pentafluoroethyl-1,1-dimethyl-3-heptynyl]-4H-inden-4-one (IId) in 4 ml of anhydrous tetrahydrofuran is added dropwise over a 10 min period. The reaction mixture is then stirred at −78° C. for 2 hrs., quenched with 2N Rochelle salt and warmed up to room temperature. The isolation of the silylated title compound can be done by extraction with ethyl acetate and purification by FLASH chromatography.

Removal of the silyl protecting group can be performed by treating a solution of the silylated title compound in 4 ml of anhydrous tetrahydrofuran with 1.25 mmole of 1M solution of tetrabutylammonium fluoride in tetrahydrofuran under argon and stirring at room temperature for 18 hrs. The reaction mixture is quenched with water and the resulting title compound is isolated by extraction with ethyl acetate and purification by FLASH chromatography.

Example 5

1α-Fluoro-25-hydroxy-16-ene-23-yne-26,27-hexafluoro-20-methyl-cholecalciferol

The title compound can be prepared by following the same experimental design as in the Example 1 and using instead of 3aR-(3aα,7aβ)-1,2,3,3a,5,6,7,7a-octahydro-7a-methyl-[6,6,6-trifluoro-5-hydroxy-5-trifluoromethyl-1,1-dimethyl-3-hexynyl]-4H-inden-4-one (IIa) the corresponding 1-ene derivative, 3aR-(3aα,7aβ)-3,3a,5,6,7,7a-hexahydro-7a-methyl-[6,6,6-trifluoro-5-hydroxy-5-trifluoromethyl-1,1-dimethyl-3-hexy-nyl]-4H-inden-4-one (IIe).

Example 6

1α-Fluoro-25-hydroxy-16-ene-23-yne-26,27-hexafluoro-20,21,28-cyclopropyl-cholecalciferol The title compound can be prepared by following the same experimental design as in the Example 2 and using instead of 3aR-(3aα,7aβ)-1,2,3,3a,5,6,7,7a-octahydro-7a-methyl-1-[8,8,8-trifluoro-7-hydroxy-7-trifluoromethyl-1,3-cyclo-5-octynyl]-4H-inden-4-one (IIb) the corresponding 1-ene derivative, 3aR-(3aα,7aβ)-3,3a,5,6,7,7a-hexahydro-7a-methyl-1-[8,8,8-trifluoro-7-hydroxy-7-trifluoromethyl-1,3-cyclo-5-octynyl]-4H-inden-4-one (Ihf).

Example 7

1α-Fluoro-25-hydroxy-16-ene-23-yne-20-methyl-26,27-bishomo-26a,27a-hexafluoro-cholecalciferol The title compound can be prepared by following the same experimental design as in the Example 4 and using instead of 3aR-(3aα,7aβ)-1,2,3,3a,5,6,7,7a-octahydro-7a-methyl-1-[6,6,7,7,7-pentafluoro-5-hydroxy-5-pentafluoroethyl-1,1-dimethyl-3-heptynyl]-4H-inden-4-one (IId) the corresponding 1-ene-hexafluoro derivative, 3aR-(3aα,7aβ)-3,3a,5,6,7,7a-hexa-hydro-7a-methyl-1-[7,7,7-trifluoro-5-hydroxy-5-trifluoroethyl-1,1-dimethyl-3-heptynyl]-4H-inden-4-one (IIg).

Example 8

1α-Fluoro-25-hydroxy-23Z-ene-26,27-hexafluoro-20-methyl-cholecalciferol

The title compound can be prepared by following the same experimental design as in the Example 1 and using instead of 3aR-(3aα,7aβ)-1,2,3,3a,5,6,7,7a-octahydro-7a-methyl-1-[6,6,6-trifluoro-5-hydroxy-5-trifluoromethyl-1,1-dimethyl-3-hexynyl]-4H-inden-4-one (IIa) the corresponding 3Z-hexenyl derivative, 3aR-(3aα,7aβ)-1,2,3,3a,5,6,7,7a-octa-hydro-7a-methyl-1-[6,6,6-trifluoro-5-hydroxy-5-trifluoromethyl-1,1-dimethyl-3Z-hexenyl]-4H-inden-4-one (IIh).

Example 9

1α-Fluoro-25-hydroxy-23Z-ene-26,27-hexafluoro-20,21,28-cyclopropyl-cholecalciferol The title compound can be prepared by following the same experimental design as in the Example 2 and using instead of 3aR-(3aα,7aβ)-1,2,3,3a,5,6,7,7a-octahydro-7a-methyl-1-[8,8,8 8-trifluoro-7-hydroxy-7-trifluoromethyl-1, 3-cyclo-5-octynyl]-4H-inden-4-one (IIb) the corresponding 5Z-octenyl derivative, 3aR-(3aα,7aβ)-1,2,3,3a,5,6,7,7a-octahydro-7a-methyl-1-[8,8,8-trifluoro-7-hydroxy-7-trifluoromethyl-1,3-cyclo-5Z-octenyl]-4H-inden-4-one (IIi).

Example 10

1α-Fluoro-25-hydroxy-20,23Z-diene-26,27-hexafluoro-cholecalciferol

The title compound can be prepared by following the same experimental design as in the Example 3 and using instead of 3aR-(3aα,7aβ)-1,2,3,3a,5,6,7,7a-octahydro-7a-methyl-1-[6,6,6-trifluoro-5-hydroxy-5-trifluoromethyl-1-methylene-3-hexynyl]-4H-inden-4-one (IIc) the corresponding 3Z-hexenyl derivative, 3aR-(3aα,7aβ)-1,2,3,3a,5,6,7,7a-octahydro-7a-methyl-1-[6,6,6-trifluoro-5-hydroxy-5-trifluoro-methyl-1-methylene-3Z-hexenyl]-4H-inden-4-one (IIj).

Example 11

1α-Fluoro-25-hydroxy-23Z-ene-20-methyl-26,27-bishomo-26,26a,27,27a-decafluoro-cholecalciferol The title compound can be prepared by following the same experimental design as in the Example 4 and using instead of 3aR-(3aα,7aβ)-1,2,3,3a,5,6,7,7a-octahydro-7a-methyl-1-[6,6,7,7,7-pentafluoro-5-hydroxy-5-pentafluoroethyl-1,1-dimethyl-3-heptynyl]-4H-inden-4-one (IId) the corresponding 3Z-heptynyl derivative, 3aR-(3aα,7aβ)-1,2,3,3a,5,6,7,7a-octahydro-7a-methyl-1-[6,6,7,7,7-pentafluoro-5-hydroxy-5-pentafluoroethyl-1,1-dimethyl-3Z-heptenyl]-4H-inden-4-one (IIk).

Example 12

1α-Fluoro-25-hydroxy-16,23Z-diene-26,27-hexafluoro-20-methyl-cholecalciferol

The title compound can be prepared by following the same experimental design as in the Example 1 and using instead of 3aR-(3aα,7aβ)-1,2,3,3a,5,6,7,7a-octahydro-7a-methyl-1-[6,6,6-trifluoro-5-hydroxy-5-trifluoromethyl-1,1-dimethyl-3-hexynyl]-4H-inden-4-one (IIa) the corresponding 1,3Z-diene derivative, 3aR-(3aα,7aβ)-3,3a,5,6,7,7a-hexahydro-7a-methyl-1-[6,6,6-trifluoro-5-hydroxy-5-trifluoromethyl-1,1-dimethyl-3Z-hexenyl]-4H-inden-4-one (IIl).

Example 13

1α-Fluoro-25-hydroxy-16,23Z-diene-26,27-hexafluoro-20,21,28-cyclopropyl-cholecalciferol The title compound can be prepared by following the same experimental design as in Example 2 and using instead of 3aR-(3aα,7aβ)-1,2,3,3a,5,6,7,7a-octahydro-7a-methyl-1-[8,8,8-trifluoro-7-hydroxy-7-trifluoromethyl-1,3-cyclo-5-octynyl]-4H-inden-4-one (IIb) the corresponding 1,5Z-diene derivative, 3aR-(3aα,7aβ)-3,3a,5,6,7,7a-hexahydro-7a-methyl-1-[8,8,8-trifluoro-7-hydroxy-7-trifluoromethyl-1,3-cyclo-5Z-octenyl]-4H-inden-4-one (IIm).

Example 14

1α-Fluoro-25-hydroxy-16,23Z-diene-20-methyl-26,27-bishomo-26a,27a-hexafluoro-cholecalciferol The title compound can be prepared by following the same experimental design as in the Example 4 and using instead of 3aR-(3aα,7aβ)-1,2,3,3a,5,6,7,7a-octahydro-7a-methyl-1-[6,6,7,7,7-pentafluoro-5-hydroxy-5-pentafluoroethyl-1,1-dimethyl-3-heptynyl]-4H-inden-4-one (IId) the corresponding 1,3Z-diene-hexafluoro derivative, 3aR-(3aα,7aβ)-3,3a,5,6,7,7a-hexahydro-7a-methyl-1-[7,7,7-trifluoro-5-hydroxy-5-trifluoroethyl-1,1-dimethyl-3Z-heptenyl]-4H-inden-4-one (IIn).

Example 15

1α-Fluoro-25-hydroxy-23E-ene-26,27-hexafluoro-20-methyl-cholecalciferol

The title compound can be prepared by following the same experimental design as in the Example 1 and using instead of 3aR-(3aα,7aβ)-1,2,3,3a,5,6,7,7a-octahydro-7a-methyl-1-[6,6,6-trifluoro-5-hydroxy-5-trifluoromethyl-1,1-dimethyl-3-hexynyl]-4H-inden-4-one (IIa) the corresponding 3E-hexenyl derivative, 3aR-(3aα,7aβ)-1,2,3,3a,5,6,7,7a-octahydro-7a-methyl-1-[6,6,6-trifluoro-5-hydroxy-5-trifluoromethyl-1,1-dimethyl-3E-hexenyl]-4H-inden-4-one (IIo).

Example 16

1α-Fluoro-25-hydroxy-23E-ene-26,27-hexafluoro-20,21,28-cyclopropyl-cholecalciferol The title compound can be prepared by following the same experimental design as in the Example 2, and using instead of 3aR-(3aα,7aβ)-1,2,3,3a,5,6,7,7a-octahydro-7a-methyl-1-[8,8,8-trifluoro-7-hydroxy-7-trifluoromethyl-1,3-cyclo-5-octynyl]-4H-inden-4-one (IIb) the corresponding 5E-octenyl derivative, 3aR-(3aα,7aβ)-1,2,3,3a,5,6,7,7a-octahydro-7a-methyl-1-[8,8,8-trifluoro-7-hydroxy-7-trifluoromethyl-1,3-cyclo-5E-octenyl]-4H-inden-4-one (IIp).

Example 17

1α-Fluoro-25-hydroxy-20,23E-diene-26,27-hexafluoro-cholecalciferol

The title compound can be prepared by following the same experimental design as in the Example 3, and using instead of 3aR-(3aα,7aβ)-1,2,3,3a,5,6,7,7a-octahydro-7a-methyl-1-[6,6,6-trifluoro-5-hydroxy-5-trifluoromethyl-1-methylene-3-hexynyl]-4H-inden-4-one (IIc) the corresponding 3E-hexenyl derivative, 3aR-(3aα,7aβ)-1,2,3,3a,5,6,7,7a-octahydro-7a-methyl-1-[6,6,6-trifluoro-5-hydroxy-5-trifluoromethyl-1-methylene-3-hexenyl]-4H-inden-4-one (IIq).

Example 18

1α-Fluoro-25-hydroxy-23E-ene-20-methyl-26,27-bishomo-26,26a,27,27a-decafluoro-cholecalciferol The title compound can be prepared by following the same experimental design as in the Example 4, and using instead of 3aR-(3aα,7aβ)-1,2,3,3a,5,6,7,7a-octahydro-7a-methyl-1-[6,6,7,7,7-pentafluoro-5-hydroxy-5-pentafluoroethyl-1,1-dimethyl-3-heptynyl]-4H-inden-4-one (IId) the corresponding 3E-heptenylderivative,3aR-(3aα,7aβ)-1,2,3,3a,5,6,7,7a-octahy-dro-7a-methyl-1-[6,6,7,7,7-pentafluoro-5-hydroxy-5-pentafluoro-1,1-di-methyl-3E-heptenyl]-4H-inden-4-one (IIr).

Example 19

1α-Fluoro-25-hydroxy-16,23E-diene-26,27-hexafluoro-20-methyl-cholecalciferol

The title compound can be prepared by following the same experimental design as in the Example 1, and using instead of 3aR-(3aα,7aβ)-1,2,3,3a,5,6,7,7a-octahydro-7a-methyl-1-[6,6,6-trifluoro-5 -hydroxy-5-trifluoroethyl -1,1-dimethyl-3 -hexynyl]-4H-inden-4-one (IIa) the corresponding 1,3E-diene derivative, 3aR-(3aα,7aβ)-3,3a,5,6,7,7a-hexahydro-7a-methyl-1-[6,6,6-trifluoro-5-hydroxy-5-trifluoromethyl-1,1-dimethyl-3E-hexenyl]-4H-inden-4-one (IIs).

Example 20

1α-Fluoro-25-hydroxy-16,23E-diene-26,27-hexafluoro-20,21,28-cyclopropyl-cholecalciferol The title compound can be prepared by following the same experimental design as in the Example 2, and using instead of 3aR-(3aα,7aβ)-1,2,3,3a,5,6,7,7a-octahydro-7a-methyl-1-[8,8,8-trifluoro-7-hydroxy-7-trifluoromethyl-1,3-cyclo-5-octynyl]-4H-inden-4-one (II*b*) the corresponding 1,5E-diene derivative, 3aR-(3aα,7aβ)-3,3a,5,6,7,7a-hexahydro-7a-methyl-1-[8,8,8-trifluoro-7-hydroxy-7-trifluoromethyl-1,3-cyclo-5E-octenyl]-4H-inden-4-one (II*t*).

Example 21

1α-Fluoro-25-hydroxy-16,23E-diene-20-methyl-26,27-bishomo-26a,27a-hexafluoro-cholecalciferol The title compound can be prepared by following the same experimental design as in the Example 4, and using instead of 3aR-(3aα,7aβ)-1,2,3,3a,5,6,7,7a-octahydro-7a-methyl-1-[6,6,7,7,7-pentafluoro-5-hydroxy-5-pentafluoroethyl-3-heptynyl]-4H-inden-4-one (II*d*), the corresponding 1,3E-diene-hexafluoro derivative, 3aR-(3aα,7aβ)-3,3a,5,6,7,7a-hexahydro-7a-methyl-1-[7,7,7-trifluoro-5-hydroxy-5-trifluoroethyl-3E-heptenyl]-4H-inden-4-one (II*u*).

Example 22

1α-Fluoro-25-hydroxy-16,20-diene-23-yne-26,27-hexafluoro-cholecalciferol

The title compound can be prepared by following the same experimental design as in the Example 3, and using instead of 3aR-(3aα,7aβ)-1,2,3,3a,5,6,7,7a-octahydro-7a-methyl-1-[6,6,6-trifluoro-5-hydroxy-5-trifluoromethyl-1-methylene-3-hexenyl]-4H-inden-4-one (II*c*), the corresponding 1-ene derivative, 3aR-(3aα,7aβ)-3,3a,5,6,7,7a-hexahydro-7a-methyl-1-[6,6,6-trifluoro-5-hydroxy-5-trifluoromethyl-1-methylene-hexynyl]-4H-inden-4-one (II*v*).

Example 23

1α-Fluoro-25-hydroxy-16,20,23Z-triene-26,27-hexafluoro-cholecalciferol

The title compound can be prepared by following the same experimental design as in the Example 3, and using instead of 3aR-(3aα,7aβ)-1,2,3,3a,5,6,7,7a-octahydro-7a-methyl-1-[6,6,6-trifluoro-5-hydroxy-5-trifluoromethyl-1-methylene-3-hexenyl]-4H-inden-4-one (II*c*), the corresponding 1,3Z-diene derivative, 3aR-(3aα,7aβ)-3,3a,5,6,7,7a-hexahydro-7a-methyl-1-[6,6,6-trifluoro-5-hydroxy-5-trifluoromethyl-1-methylene-3Z-hexenyl]-4H-inden-4-one (II*w*).

Example 24

1α-Fluoro-25-hydroxy-16,20,23E-triene-26,27-hexafluoro-cholecalciferol

The title compound can be prepared by following the same experimental design as in the Example 3, and using instead of 3aR-(3aα,7aβ)-1,2,3,3a,5,6,7,7a-octahydro-7a-methyl-1-[6,6,6-trifluoro-5-hydroxy-5-trifluoromethyl-1-methylene-3-hexynyl]-4H-inden-4-one (II*c*), the corresponding 1,3E-diene derivative, 3aR-(3aα,7aβ)-3,3a,5,6,7,7a-hexahydro-7a-methyl-[6,6,6-trifluoro-5-hydroxy-5-trifluoromethyl-1-methylene-3E-hexenyl]-4H-inden-4-one (II*z*).

Example 25

1α-Fluoro-25-hydroxy-23E-ene-26,27-hexafluoro-20,21,28-cyclopropyl-19-nor-cholecalciferol The title compound can be prepared by the following procedure:

To a solution of 1.5 mmole (3R-(3α,5β,Z)]-2-[2-[3-fluoro-5[[(1,1-dimethyl-ethyl)dimethylsilyl]oxy]cyclohexylidene]ethyl] diphenyl phosphine oxide (15) in 9 ml anhydrous tetrahydrofuran at −78° C. is added 1.5 mmole of 1.6M n-butyllithium in hexane dropwise in an argon atmosphere. After stirring for 5 minutes, a solution of 0.6 mmole 3aR-(3aα,7aβ)-1,2,3,3a,5,6,7,7a-octahydro-7a-methyl-1-[8,8,8-trifluoro-7-hydroxy-7-tri-fluoromethyl-1,3-cyclo-5E-octenyl]-4H-inden-4-one (II*p*) in 4 ml of anhydrous tetrahydrofuran is added dropwise over a 10 min period. The reaction mixture is then stirred at −78° C. for 2 hours, quenched with 2N Rochelle salt and warmed up to a room temperature. The isolation of the silylated title compound can be done by extraction with ethyl acetate and purification by FLASH chromatography.

Removal of the silyl protecting group can be performed by treating a solution of the silylated title compound in 4 ml of anhydrous tetrahydrofuran with 1.25 mmole of 1M solution of tetrabutylammonium fluoride in tetrahydrofuran under argon and stirring at room temperature for 18 hrs. This reaction mixture is quenched with water and the resulting title compound is isolated by extraction with ethyl acetate and purification by FLASH chromatography.

It will be recognized by those skilled in the art that there are different variations of these syntheses or alternative synthetic methods which are well known in the art that may be employed to achieve some steps in the syntheses detailed above.

Example 26

Bone anabolism in the rat

The compounds of the present invention are more effective than 1,25-dihydroxy vitamin $D_3$ at bone accretion and do not induce hypercalciuria, nephrotoxicity, or hypercalcemia at therapeutically effective doses. This has been demonstrated as follows:

Three month old rats are ovariectomized (Ovx) and administered either 1,25-dihydroxy vitamin $D_3$ (vit. D in Table) or one of the compounds of the present invention once a day by mouth starting at 3 weeks post-ovariectomy and continuing until final sacrifice at 6 weeks post-ovariectomy. Control groups, both sham (rats that were not ovariectomized) and Ovx, received vehicle only. Blood and urine samples were collected twice, at 4 weeks post-ovariectomy and again at the 6 week mark and the amount of serum and urine calcium was determined. The final femoral calcium determined upon sacrifice 6 weeks post-ovariectomy.

The bone mineral density of the right femur was determined by using a High Resolution Software Package on a QDR-1000W Bone Densitometer™ (Hologic, Walthan, Mass.). The animals were scanned by placing them on a scanning block in a supine position such that the right leg was perpendicular to the main body and the tibia was perpendicular to the femur.

The increase in the bone mineral density and the amount of calcium in the urine and the serum for some of the compounds of this invention in this assay are given in the table below:

| CPD # | Surgery | Treatment | Dose μg/kg | Whole Fermur BMD mg/cm² | Serum Calcium g/dl (6th wk) | Urine Calcium/ Creatinine mg/dl (6th wk) |
|---|---|---|---|---|---|---|
| 57 | Sham | Vehicle | 0.00 | 0.249 | 10.41 | 0.40 |
|  | Ovx | Vehicle | 0.00 | 0.23 | 9.81 | 0.26 |
|  | Ovx | Vit D | 0.20 | 0.2370 | 10.21 | 1.35 |
|  | Ovx | Cpd. 57 | 1.50 | 0.248a | 10.12 | 0.90 |
| 58 | Sham | Vehicle | 0.00 | 0.251 | 9.27 | 0.35 |
|  | Ovx | Vehicle | 0.00 | 0.228 | 9.70 | 0.29 |
|  | Ovx | Vit D | 0.20 | 0.233 | 10.93a | 1.44 |
|  | Ovx | Cpd. 58 | 5.00 | 0.236a | 9.46 | 0.63 |
|  | Sham | Vehicle | 0.00 | 0.244 | 8.74 | 0.38 |
| 59 | Ovx | Vehicle | 0.00 | 0.233 | 8.81 | 0.30 |
|  | Ovx | Vit. D | 0.20 | 0.235 | 9.51a | 0.76 |

-continued

| CPD # | Surgery | Treatment | Dose µg/kg | Whole Fermur BMD mg/cm$^2$ | Serum Calcium g/dl (6th wk) | Urine Calcium/ Creatinine mg/dl (6th wk) |
|---|---|---|---|---|---|---|
| | Ovx | Cpd. 59 | 2.00 | 0.233 | 9.20 | 0.35 |
| | Sham | Vehicle | 0.00 | 0.255 | 9.09 | 0.23 |
| 60 | Ovx | Vehicle | 0.00 | 0.234 | 9.54 | 0.17 |
| | Ovx | Vit. D | 0.20 | 0.240 | 10.64a | 1.44 |
| | Ovx | Cpd. 60 | 0.10 | 0.242 | 9.59 | 0.52 |
| | Sham | Vehicle | 0.00 | 0.239 | 9.20 | 0.31 |
| 61 | Ovx | Vehicle | 0.00 | 0.224 | 9.31 | 0.27 |
| | Ovx | Vit. D | 0.20 | 0.239a | 10.61a | 1.48 |
| | Ovx | Cpd. 61 | 0.50 | 0.243a | 10.68a | 1.34 | a = Significant difference (p < 0.05), Cpd. or Vit. D vs Ovx vehicle.

As seen above the compounds of this invention, in general, increase the bone mineral density but show reduced calciuria and calcemia than 1,25-di(OH) vitamin D.

Example 27

Oral dosage form soft gelatin capsule

A capsule for oral administration is formulated under nitrogen in amber light from 0.01 to 25.0 µg of one of the compounds of the present invention in 150 mg of fractionated coconut oil, with 0.015 mg butylated hydroxytoluene (BHT) and 0.015 mg butylated hydroxyanisole (BHA), filled in a soft gelatin capsule.

The foregoing invention has been described in some detail by way of illustration and example, for the purposes of clarity and understanding. It will be obvious to one of ordinary skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, patent applications and publications cited in this application are hereby incorporated by reference in their entirety for all purposes to the same extent as if each individual patent, patent application or publication were so individually denoted.

We claim:

1. A compound of the Formula

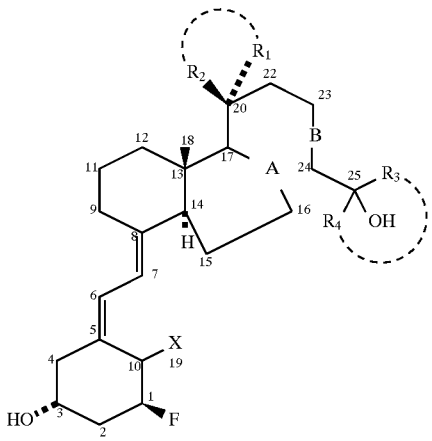

(I)

wherein:

X is hydrogen or $=CH_2$;

$R_1$ and $R_2$ are, independently of each other, hydrogen, $(C_1-C_4)$ alkyl or fluoroalkyl, or $R_1$ and $R_2$ together with C-20 form a $(C_3-C_6)$ cycloalkyl or cyclofluoroalkyl, or $R_1$ and $R_2$ together form $=CH_2$;

$R_3$ and $R_4$ are, independently of each other, a $(C_1-C_4)$ alkyl or fluoroalkyl, or $R_3$ and $R_4$ together with C-25 form a $(C_3-C_9)$ cycloalkyl or cyclofluoroalkyl;

A is a single bond or a double bond; and

B is a double bond or a triple bond;

except that:

(i) when X is $=CH_2$, $R_3$ and $R_4$ are each $CF_3$, A is a double bond and one of $R_1$ or $'R_2$ is hydrogen, then the other of $R_1$ or $R_2$ cannot be $CH_3$;

(ii) when X is $=CH_2$, $R_3$ and $R_4$ are each a $(C_1-C_2)$ alkyl, A is a double bond and $R_2$ is hydrogen, then $R_1$ cannot be $CH_3$;

(iii) when X is $=CH_2$, $R_3$ and $R_4$ are each a $(C_1-C_4)$ alkyl, A is a double bond and $R_1$ is hydrogen, then $R_2$ cannot be $CH_3$;

(iv) when X is $=CH_2$, one of $R_3$ or $R_4$ is a $CF_3$, A is a double bond, $R_1$ is CH3 and $R_2$ is hydrogen, then the other of $R_3$ or $R_4$ cannot be $CH_3$; and (v) when X is hydrogen, $R_3$ and $R_4$ are each $CF_3$, A is a double bond, B is a triple bond and $R_2$ is hydrogen, then $R_1$ cannot be $CH_3$.

2. The compound of claim 1, wherein:

X is hydrogen or $=CH_2$;

$R_1$ and $R_2$ are, independently of each other, selected from the group consisting of hydrogen, $CH_3$ or $CF_3$;

$R_3$ and $R_4$ are, independently of each other, selected from the group consisting of $CH_3$, $CF_3$, $CH2CH_3$, $CH_2CF_3$, $CF_2CH_3$ and $CF_2CF_3$;

A is a single bond or a double bond; and

B is a double bond or a triple bond.

3. The compound of claim 1, wherein:

X is hydrogen or $=CH_2$;

$R_1$ and $R_2$ together with C-20 form a cyclopropano, cyclodifluoropropano or cyclotetrafluoropropano group;

$R_3$ and $R_4$ are, independently of each other, selected from the group consisting of $CH_3$, $CF_3$, $CH_2CH_3$, $CH_2CF_{31}$ $CF_2CH_3$ and $CF_2CF_3$;

A is a single bond or a double bond; and

B is a double bond or a triple bond.

4. The compound of claim 1, wherein:

X is hydrogen or $=CH_2$;

$R_1$ and $R_2$ together form $=CH_2$;

$R_3$ and $R_4$ are, independently of each other, selected from the group consisting of $CH_3$, $CF_3$, $CH_2CH_3$, $CH_2CF_3$, $CF_2CH_3$ and $CF_2CF_3$;

A is a single bond or a double bond; and

B is a double bond or a triple bond.

5. The compound of claim 1, wherein:

X is hydrogen or $=CH_2$;

$R_1$ and $R_2$ are, independently of each other, selected from the group consisting of hydrogen, $CH_3$ or $CF_3$;

$R_3$ and $R_4$ together with C-25 form a cyclopentano, cyclodifluoropentano, cyclotetrafluoropentano, cyclohexafluoropentano, cyclooctafluoropentano, cyclohexano, cyclodifluorohexano, cyclotetrafluorohexano, cyclohexafluorohexano or cyclooctafluorohexano group;

A is a single bond or a double bond; and

B is a double bond or a triple bond.

6. The compound of claim 1, wherein:

X is hydrogen or $=CH_2$;

$R_1$ and $R_2$ together with C-20 form a cyclopropano, cyclodifluoropropano or cyclotetrafluoropropano group;

$R_3$ and $R_4$ together with C-25 form a cyclopentano, cyclodifluoropentano, cyclotetrafluoropentano, cyclohexafluoropentano, cyclooctafluoropentano, cyclohexano, cyclodifluorohexano, cyclotetrafluorohexano, cyclohexafluorohexano or cyclooctafluorohexano group;

A is a single bond or a double bond; and

B is a double bond or a triple bond.

7. The compound of claim 1, wherein:

X is hydrogen or $=CH_2$;

$R_1$ and $R_2$ together form $=CH2$;

$R_3$ and $R_4$ together with C-25 form a cyclopentano, cyclodifluoropentano, cyclotetrafluoropentano, cyclohexafluoropentano, cyclooctafluoropentano, cyclohexano, cyclodifluorohexano, cyclotetrafluorohexano, cyclohexafluorohexano or cyclooctafluorohexano group;

A is a single bond or a double bond; and

B is a double bond or a triple bond.

8. The compound of claim 2, wherein:

X is $=CH2$;

$R_1$ and $R_2$ are, independently of each other, selected from the group consisting of hydrogen, $CH_3$ or $CF_3$;

$R_3$ and $R_4$ are, independently of each other, selected from the group consisting of $CH_3$, $CF_3$, $CH_2CH_3$, $CH_2CF_3$, $CF_2CH_3$ and $CF_2CF_3$;

A is a single bond or a double bond; and

B is a double bond or a triple bond.

9. The compound of claim 8, wherein:

$R_1$ and $R_2$ are each $CH_3$;

$R_3$ and $R_4$ are, independently of each other, $CF_3$;

A is a double bond; and

B is a triple bond.

10. The compound of claim 3, wherein:

X is $=CH_2$;

$R_1$ and $R_2$ together with C-20 form a cyclopropano, cyclodifluoropropano or cyclotetrafluoropropano group;

$R_3$ and $R_4$ are, independently of each other, selected from the group consisting of $CH_3$, $CF_3$, $CH_2CH_3$, $CH_2CF_3$, $CF_2CH_3$ and $CF_2CF_3$;

A is a single bond or a double bond; and

B is a double bond or a triple bond.

11. The compound of claim 10, wherein:

$R_1$ and $R_2$ together with C-20 form a cyclopropano group;

$R_3$ and $R_4$ are each $CF_3$;

A is a double bond; and

B is a triple bond.

12. The compound of claim 4, wherein:

X is $=CH_2$;

$R_3$ and $R_4$ are, independently of each other, selected from the group consisting of $CH_3$, $CF_3$, $CH_2CH_3$, $CH_2CF_3$, $CF_2CH_3$ and $CF_2CF_3$;

A is a single bond or a double bond; and

B is a double bond or a triple bond.

13. The compound of claim 12, wherein:

$R_3$ and $R_4$ are each $CF_3$;

A is a double bond; and

B is a triple bond.

14. The compound of claim 5, wherein:

X is $=CH_2$;

$R_1$ and $R_2$ are, independently of each other, selected from the group consisting of hydrogen, $CH_3$ or $CF_3$;

$R_3$ and $R_4$ together with C-25 form a cyclopentano, cyclodifluoropentano, cyclotetrafluoropentano, cyclohexafluoropentano, cyclooctafluoropentano, cyclohexano, cyclodifluorohexano, cyclotetrafluorohexano, cyclohexafluorohexano or cyclooctafluorohexano group;

A is a single bond or a double bond; and

B is a double bond or a triple bond.

15. The compound of claim 14, wherein:

$R_1$ and $R_2$ are each $CF_3$;

$R_3$ and $R_4$ together with C-25 form a cyclopentano group;

A is a double bond; and

B is a triple bond.

16. The compound of claim 6, wherein:

X is $=CH_2$;

$R_1$ and $R_2$ together with C-20 form a cyclopropano, cyclodifluoropropano or cyclotetrafluoropropano group;

$R_3$ and $R_4$ together with C-25 form a cyclopentano, cyclodifluoropentano, cyclotetrafluoropentano, cyclohexafluoropentano, cyclooctafluoropentano, cyclohexano, cyclodifluorohexano, cyclotetrafluorohexano, cyclohexafluorohexano or cyclooctafluorohexano group;

A is a single bond or a double bond; and

B is a double bond or a triple bond.

17. The compound of claim 7, wherein:

X is $=CH_2$;

$R_3$ and $R_4$ together with C-25 form a cyclopentano, cyclodifluoropentano, cyclotetrafluoropentano, cyclohexafluoropentano, cyclooctafluoropentano, cyclohexano, cyclodifluorohexano, cyclotetrafluorohexano, cyclohexafluorohexano or cyclooctafluorohexano group;

A is a single bond or a double bond; and

B is a double bond or a triple bond.

18. A pharmaceutical composition comprising a pharmaceutically acceptable carrier and a compound of formula (I), wherein:

X is hydrogen or $=CH_2$;

$R_1$ and $R_2$ are, independently of each other, hydrogen, $(C_1-C_4)$ alkyl or fluoroalkyl, or $R_1$ and $R_2$ together with C-20 form a $(C_3-C_5)$ cycloalkyl or cyclofluoroalkyl, or $R_1$ and $R_2$ together form $=CH_2$;

$R_3$ and $R_4$ are, independently of each other, a $(C_1-C_4)$ alkyl or fluoroalkyl, or $R_3$ and $R_4$ together with C-25 form a $(C_3-C_9)$ cycloalkyl or cyclofluoroalkyl;

A is a single bond or a double bond; and

B is a double bond or a triple bond;

except that:

(i) when X is $=CH_2$, $R_3$ and $R_4$ are each $CF_3$, A is a double bond and one of $R_1$ or $R_2$ is hydrogen, then the other of $R_1$ or $R_2$ cannot be $CH_3$;

(ii) when X is $=CH_2$, $R_3$ and $R_4$ are each a $(C_1-C_2)$ alkyl, A is a double bond and $R_2$ is hydrogen, then $R_1$ cannot be $CH_3$;

(iii) when X is $=CH_2$, $R_3$ and $R_4$ are each a $(C1-C_4)$ alkyl, A is a double bond and $R_1$ is hydrogen, then $R_2$ cannot be $CH_3$;

(iv) when X is $=CH_2$, one of $R_3$ or $R_4$ is a $CF_3$, A is a double bond, $R_1$ is $CH_3$ and $R_2$ is hydrogen, then the other of $R_3$ or $R_4$ cannot be $CH_3$; and (v) when X is hydrogen, $R_3$ and $R_4$ are each $CF_3$, A is a double bond, B is a triple bond and $R_2$ is hydrogen, then $R_1$ cannot be $CH_3$.

19. A method for treating osteoporosis via administration of a therapeutically effective amount of a compound of formula (I), wherein:

X is hydrogen or $=CH_2$;

$R_1$ and $R_2$ are, independently of each other, hydrogen or $(C_1-C_4)$ alkyl or fluoroalkyl, or $R_1$ and $R_2$ together with C-20 form a $(C_3-C_6)$ cycloalkyl or cyclofluoroalkyl, or one of $R_1$ and $R_2$ together form $=CH_2$;

$R_3$ and $R_4$ are, independently of each other, a $(C_1-C_4)$ alkyl or fluoroalkyl, or $R_3$ and $R_4$ together with C-25 form a $(C_3-C_9)$ cycloalkyl or cyclofluoroalkyl;

A is a single bond or a double bond; and

B is a double bond or a triple bond;

except that where $R_3$ and $R_4$ are each $CF_3$ and A is a double bond and B is a triple bond and $R_2$ is hydrogen, then $R_1$ cannot be $CH_3$.

20. The method of claim 19, wherein the therapeutically effective amount of the compound is from about 0.0002 μg compound/kg body weight/day to about 0.5 μg compound/kg body weight/day.

21. The method of claim 19, wherein the therapeutically effective amount of the compound is from about 0.05 μg/day to about 10 μg/day.

22. The method of claim 21, wherein the compound is administered to a human female.

23. The method of claim 22, wherein the compound is administered once a day.

24. The method of claim 19, wherein:

X is $=CH_2$;

one of $R_1$ and $R_2$ is hydrogen and the other is $(C_1-C_4)$ alkyl;

$R_3$ and $R_4$ are $(C_1-C_4)$ alkyl;

A is a double bond; and

B is a double bond.

25. The method of claim 24, wherein:

$R_1$ is hydrogen;

$R_2$ is $CH_3$;

$R_3$ and $R_4$ are ethyl; and

B is a trans double bond.

26. The method of claim 24, wherein:

$R_1$ is $CH_3$;

$R_2$ is hydrogen;

$R_3$ and $R_4$ are ethyl; and

B is a trans double bond.

27. A compound of Formula (II)

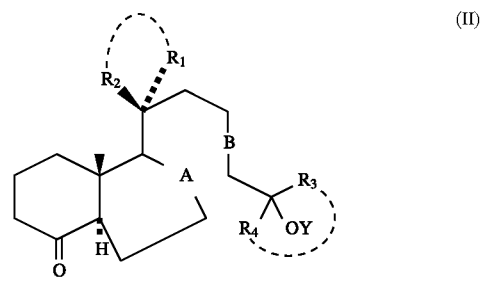

(II)

wherein:

$R_1$ and $R_2$ are
(a) both methyl,
(b) together with the carbon to which they are attached form a cyclopropane ring, or
(c) form a $=CH_2$;

$R_3$ and $R_4$ are, independently of each other, a $(C_1-C_4)$ alkyl or fluoroalkyl, or $R_3$ and $R_4$ together with C-25 form a $(C_3-C_9)$ cycloalkyl or cyclofluoroalkyl;

A is a single bond or a double bond;

B is a double bond or a triple bond; and

Y is H or $OSiMe_3$.

* * * * *